(12) United States Patent
Chepuri et al.

(10) Patent No.: US 9,994,602 B2
(45) Date of Patent: Jun. 12, 2018

(54) SPIROANNULATED NUCLEOSIDES AND PROCESS FOR THE PREPARATION THEREOF

(71) Applicant: Council of Scientific & Industrial Research, New Delhi (IN)

(72) Inventors: Venkata Ramana Chepuri, Pune (IN); Mangesh Pandurang Dushing, Pune (IN)

(73) Assignee: COUNCIL OF SCIENTIFIC & INDUSTRIAL RESEARCH, New Delhi (IN)

( * ) Notice: Subject to any disclaimer, the term of this patent is extended or adjusted under 35 U.S.C. 154(b) by 0 days. days.

(21) Appl. No.: 15/060,285

(22) Filed: Mar. 3, 2016

(65) Prior Publication Data

US 2016/0185811 A1 Jun. 30, 2016

Related U.S. Application Data

(62) Division of application No. 13/976,872, filed as application No. PCT/IB2011/055968 on Dec. 27, 2011, now Pat. No. 9,346,847.

(30) Foreign Application Priority Data

Dec. 27, 2010 (IN) .............. 3103/DEL/2010

(51) Int. Cl.
 *C07H 1/00* (2006.01)
 *C07H 19/16* (2006.01)
 *C07H 19/06* (2006.01)

(52) U.S. Cl.
 CPC ............... *C07H 1/00* (2013.01); *C07H 19/06* (2013.01); *C07H 19/16* (2013.01)

(58) Field of Classification Search
 CPC ........... C07H 1/00; C07H 19/16; C07H 19/06
 See application file for complete search history.

(56) References Cited

PUBLICATIONS

Wuts et al., Greene's Protective Groups in Organic Synthesis, 2007, Wiley-Interscience, 4th ed, p. 1-366.*
Suryawanshi S. B. et al. (2010) "The isochroman- and 1,3-dihydroisobenzofuran-annulation on carbohydrate templates via [2+2+2+]-cyclotrimerization and synthesis of some tricyclic nucleosides", Tetrahedron, Elsevier Science Publishers, Amsterdam, NL, vol. 66, No. 32, pp. 6085-6096.
Mangesh P., Dushing et al. (2011) "Target cum flexibility: The synthesis of C(3')-spiroannulated nucleosides", Tetrahedron Letters, vol. 52, No. 36, pp. 4627-4630.
International Search Report and Written Opinion; PCT/IB2011/055968; dated May 2, 2012.
Chu, C.K., ed., Antiviral Nucleosides: Chiral Synthesis and Chemotherapy, 2003, Elsevier Science, 1st edition, p. 1-76.

* cited by examiner

*Primary Examiner* — Jonathan S Lau
(74) *Attorney, Agent, or Firm* — Westman, Champlin & Koehler, P.A.; Z. Peter Sawicki; Visala C. Goswitz

(57) ABSTRACT

We claim a simple strategy for the synthesis of a collection of C(3')-spirodihydroisobenzo-furannulated and C(3')-spirodihydroisobenzo-furannulated nucleosides featuring a [2+2+2]-cyclotrimerization as the key reaction. The cyclotrimerization reactions are facile with the unprotected nucleosides having a diyne unit. When both alkynes of the diyne are terminal, the regioselectivity is poor. However, when one of the terminal alkynes is additionally substituted, the cyclotrimerizations are highly diastereoselective. Since the key bicycloannulation is the final step, this strategy provides flexibility in terms of the alkynes and is thus amenable for the synthesis of a focussed small molecule library.

15 Claims, 2 Drawing Sheets

SPIROANNULATED NUCLEOSIDES AND PROCESS FOR THE PREPARATION THEREOF

CROSS REFERENCE TO RELATED APPLICATIONS

This Application is a divisional of U.S. patent application Ser. No. 13/976,872, filed Jun. 27, 2013, which is a Section 371 National Stage Application of International Application No. PCT/IB2011/055968, filed Dec. 27, 2011 and published as WO/2012/090155 A1 on Jul. 5, 2012, in English, which claims priority of Indian Application No. 3103/DEL/2010, filed Dec. 27, 2010, the contents of which are hereby incorporated by reference in their entirety.

FIELD OF INVENTION

The present invention relates to Spiroannulated Nucleosides and process for the preparation thereof. More particularly, the present invention provides a library of synthetically prepared spiroannulated nucleosides as potential anti-cancer and anti-viral candidates.

BACKGROUND AND PRIOR ART

Nucleosides are glycosylamines consisting of a nucleobase (often referred to as simply base) bound to a ribose or deoxyribose sugar via a beta-glycosidic linkage. In medicine several nucleoside analogues are used as antiviral or as anticancer agents. Number of nuclear modifications has been reported in the literature in which the sugar moiety is locked in a certain conformation. However, access to collections of the distinctive small molecules by modification of the sugar moiety in a nucleoside is an important feature in the realm of chemical genetics and for identifying new therapeutic candidates.

Diversity oriented synthesis (DOS) conceptualized by Schreiber has certainly provided an impetus to rapidly accessing the complex small-molecule libraries. However, flexibility in modulating the structural characteristics remains the cornerstone of a successful hit to lead exploration. A strategy that integrates the conceptual advantages of DOS and the manipulation of chemical functionality in a target oriented synthesis could be a valuable tool in new drug discovery programs.

Designing a new class of conformationally restricted nucleosides based on modification of the glycosyl moiety by spirocyclicannulation has now been recognized as an attractive strategy for delivering molecular diversity.

In this respect, cycloaddition reactions particularly [2+2+2] alkynecyclotrimerization reaction in presence of a transition metal catalyst on sugar templates have been studied and considered to be strategically useful for synthesizing library of small molecules. The unique characteristic property of [2+2+2]-alkynecyclotrimerization is its high synthetic efficiency (with the formation of several C—C and/or C-heteroatom bonds in a single step), complete atom-economy, and the availability of a wide range of catalysts that can tolerate a myriad of protecting/functional groups.

Utilizing [2+2+2]-alkyne cyclotrimerization for building modified sugar (spiro)-annulated tricyclic homochiral scaffold and further utilization of these scaffolds for the synthesis of tricyclic nucleosides remains an important therapeutic approach for developing small molecules that control genetic disorders or infections.

Cyclotrimerization reaction on sugar templates has been less explored and limited mainly to the synthesis of C-aryl glycosides. [McDonald, F. E.; Zhu, H. Y. H.; Holmquist, C. R. J. Am. Chem. Soc. 1995, 117, 6605-6606; Yamamoto, Y.; Saigoku, T.; Ohgai, T.; Nishiyamaa, H.; Itohb, K. Chem. Commun. 2004, 2702-2703; Yamamoto, Y.; Hashimoto, T.; Hattori, K.; Kikuchi, M.; Nishiyama, H. Org. Lett. 2006, 8, 3565-3568; Novak, P.; Pohl, R.; Kotora, M.; Hocek, M. Org. Lett. 2006, 8, 2051-2054]. An early example in this context is an expedient synthesis of spirocyclic C-arylglycoside whose frame work is closely related to that of papulacandins by McDonald and co-workers [McDonald, F. E.; Zhu, H. Y. H.; Holmquist, C. R. J. Am. Chem. Soc. 1995, 117, 6605-6606]. Yamamoto and co-workers [Yamamoto, Y.; Saigoku, T.; Ohgai, T.; Nishiyamaa, H.; Itohb, K. Chem. Commun. 2004, 2702-2703; Yamamoto, Y.; Hashimoto, T.; Hattori, K.; Kikuchi, M.; Nishiyama, H. Org. Lett. 2006, 8, 3565-3568] and Kotora and co-workers [Kotora, M.; Hocek, M. Org. Lett. 2006, 8, 2051-2054] have independently reported a [2+2+2]-alkynecyclotrimerization approach for the synthesis of C-aryl ribosides and C-aryldeoxyribosides, respectively. A [2+2+2]-alkynecyclotrimerization on a sugar derived building block for constructing enantiomeric tricyclicmolecular skeletons consisting of isochroman units is disclosed by Ramana, C. V.; Suryawanshi, S. B. *Tetrahedron Lett.* 2008, 49, pg 445448.

Article titled "Carbohydrate-Based Molecular Scaffolding" by Ingrid Velter et. al in Journal of Carbohydrate Chemistry, 25:97-138, 2006 having DOI: 10.1080/07328300600733020 discloses the use of modified carbohydrates, such as sugar amino acids (SAA), iminosugars and polycyclic derivatives, as scaffolds for the generation of bioactive compounds, and the use of carbohydrates as building blocks or ligands for the production of polymers for biomedical applications.

Article titled "A simple cobalt catalyst system for the efficient and regioselective cyclotrimerisation of alkynes" by Gerhard Hilt et. al in Chem. Commun., 2005, 1474-1475 having DOI: 10.1039/b417832g describes the intermolecular cyclotrimerisation of terminal and internal alkynes catalysed by simple cobalt complexes such as a CoBr2 (diimine) under mild reaction conditions when treated with zinc and zinc iodide with high regioselectivity in excellent yields.

Article titled "Selective synthesis of C-arylglycosides via CpRuCl-catalyzed partially intramolecular cyclotrimerizations of C-alkynylglycosides" by Y. Yamamoto, T. Saigoku, in Org. Biomol. Chem, 2005, 3, 1768-1775 having DOI: 10.1039/b503258j describes synthesis of C-arylglycosides by means of the CpRuCl-catalyzed [2+2+2]-cycloaddition of α,ω-diynes with C-alkynylglycosides under mild reaction conditions. The functional group compatibility of the ruthenium catalysis towards a wide variety of functional groups allows synthesis of interesting C-arylglycosides including anthraquinone C-glycosides, bis(C-glycosyl) benzenes as well as C-arylglycoside amino acids.

Article titled "Chemo- and regioselective crossed alkyne cyclotrimerisation of 1,6-diynes with terminal monoalkynes mediated by Grubbs' catalyst or Wilkinson's catalyst" by Bernhard Witulski et. al in Chem. Commun., 2000, 1965-1966 having DOI: 10.1039/b005636g; discloses crossed alkyne cyclotrimerisations mediated by Grubbs' catalyst [RuCl$_2$(NCHPh)(PCy$_3$)$_2$] which allows the efficient synthesis of 4,6-substituted indolines with high regioselectivity, and is complementary to alkyne cyclotrimerisations mediated by Wilkinson's catalyst [RhCl(PPh$_3$)$_3$] allowing the regioselective synthesis of the corresponding 4,5-substituted isomers.

Several approaches are documented for the modification of nucleosides.

Article titled "Preparation of Highly Substituted 6-Arylpurine Ribonucleosides by Ni-Catalyzed Cyclotrimerization. Scope of the Reaction" by Pavel Turek et. al in J. Org. Chem., 2006, 71, 8978-8981 having DOI: 10.1021/jo061485y describes transition metal complex catalyzed cocyclotrimerization of protected alkynyl purine ribonucleosides with various diynes to give series of 6-arylpurine nucleosides that were further deprotected to free nucleosides. Cyclotrimerizations were obtained with a catalytic system Ni(cod)2/2PPh3. CoBr(PPh3)3 is employed as a catalyst for cyclotrimerization of with dipropargyl ether. In addition, Ni catalysis is used for direct cyclotrimerization of unprotected alkynylpurineribonucleosides to the corresponding 6-arylpurinylribosides.

Article titled "Synthesis of C-Aryldeoxyribosides by [2+2+2]-Cyclotrimerization Catalyzed by Rh, Ni, Co, and Ru Complexes" by PetrNovák, et. al in Org. Lett., 2006, 8, 2051-2054 having DOI:10.1021/o1060454m describes a novel approach to the synthesis of functionalized C-nucleosides wherein cyclotrimerization of C-alkynyldeoxyriboside with a variety of substituted 1,6-heptadiynes is carried out to obtain the corresponding C-aryldeoxyribosides in presence of catalysts selected from various transition metal complexes (Rh, Ir, Co, Ru, and Ni) preferably, $RhCl(PPh_3)_3$.

Article titled "The isochroman- and 1,3-dihydroisobenzofuran-annulation on carbohydrate templates via [2+2+2]-cyclotrimerization and synthesis of some tricyclic nucleosides" Tetrahedron, 2010, 66, pg 6085. discloses the feasibility of cyclotrimerization of sugar derived diynes and shown that the resultant products can be transformed to the tricyclic and C(3')-spirobenzoisofuran-annulated nucleosides following a sequence of chemical transformations. However, the spiro-annulated nucleosides reported contains a pentopyranose unit (6-membered sugar unit). Also, this strategy is not sufficiently effective as the number of compounds to be accessed is restricted by the limited number of nucleobases available which are introduced at the penultimate step of the synthesis. In addition, it may require additional steps if one intends to place sensitive functional groups on the isobenzofuran ring. This has prompted us to look for an alternative approach which can effectively address the library size and the ease of alteration of the functional groups on the isobenzofuran ring. This has led us into the exploration of the key C(3')-spiroannulation as the final step by means of [2+2+2]-cyclotrimerization of completely free nucleoside-diynes with alkynes which is the main theme of the current patent application and also we address the selective synthesis of spiroannulated nucleosides having the furanoside ring also.

The prior art approaches, however, have in general been executed in a target oriented way (one scheme one nucleoside). This causes a serious limitation in the collection of spironucleosides as each modification needs to be attended separately from the beginning of the synthesis.

OBJECTIVE OF THE PRESENT INVENTION

The main objective of the present invention relates to Spiroannulated Nucleosides and process for the preparation thereof.

Another object of the present invention is to develop a strategy that amply provides the spiro-annulation on sugar unit of nucleosides with enormous flexibility to modulate the substituents and properties of the newly annulated bicyclic ring systems.

Another object of the present invention is to provide spiroannulation on the sugar unit of nucleoside template involving intermolecular [2+2+2] cyclotrimerisation of the penultimate nucleoside diyne with easily accessible alkynes.

Another object of the present invention is to provide a process for the preparation of Spiroannulated Nucleosides.

Yet another object of the present invention is to obtain a library of synthetically prepared spiroannulated nucleosides.

Another object of the invention is to append the isochroman or dihydroisobenzofuran structural unit on the sugar template of the nucleoside by spiroannulation.

Another object of the current invention is to apply a structurally simplifying transform(s) at the beginning of the retrosynthetic scheme which comprises multiple bond disconnections resulting in a couple of retrons.

SUMMARY OF INVENTION

Accordingly, the present invention provides library of spiroannulated Nucleosides and process for the preparation thereof. The present invention relates to intermolecular [2+2+2] cyclotrimerization reaction of the penultimate nucleoside diynes with symmetrical or unsymmetrical alkynes to obtain enantiopure tricyclic systems of the general Formula I;

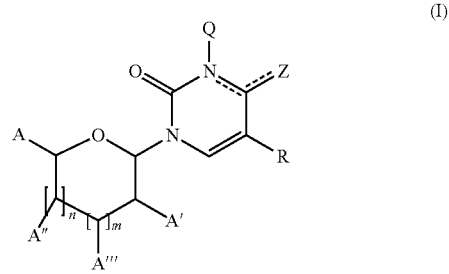

(I)

where, R (in the base) is selected from H, $C_1$-$C_4$ alkyl, halogen, OR NHR' (R'=H, $COCH_3$, $CO_2{}^tBu$); Q=H with the proviso that C—N double bond is absent, C—Z double bond is present and Z is O; Z is $NH_2$ with the proviso that C—Z double bond is absent, Q≠H; Z is O with the proviso that C—N double bond is absent;

A and A' are selected from H, lower alkyl, —OH, —OAc $CH_2OH$, —$CH_2OAc$, —$CH_2OPiv$, —$CH_2OTBS$; m and n are integers 0,1

A″ and A‴ are selected from 1,3-dihydroisobenzofuran (1a) or isochroman [3,4-dihydro-1H-benzo[c]pyran] represented by the formula (1b),

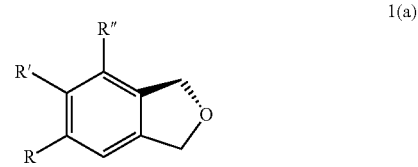

1(a)

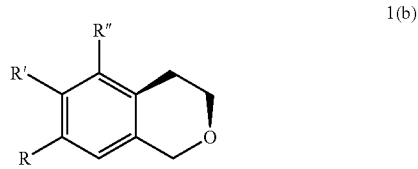

1(b)

where R, R', R" are selected from H, —OH, halo group, —CH$_2$OH, —CH$_2$OAc, —COOH, —COOMe, C1-C30 straight or branched alkyl group, optionally substituted with halogen or —OH or —NH$_2$ or —NPhth; phenyl group optionally substituted with halogen, amino, nitro, C1-C6 alkyl;

with the proviso that when n=1[i.e(CH$_2$)n=1] and where m=0[i.e(CH$_2$)m=0], A'" is absent and A" is 1,3-dihydro isobenzofuran (1a) or isochroman [3,4-dihydro-1H-benzo[c]pyran] represented by the formula (1b), directly annulated at C-3, A and A' are selected from H, lower alkyl, —OH, —OAc, —CH2OH—CH$_2$OAc, —CH$_2$OPiv, —CH$_2$OTBS; and R, R' and R" in 1,3-dihydro isobenzofuran (1a) or isochroman [3,4-dihydro-1H-benzo[c]pyran] represented by the formula (1b) are selected from H, —OH, halo group, —CH$_2$OH, —CH$_2$OAc, —COOH, —COOMe, C1-C30 straight or branched alkyl group, optionally substituted with halogen or —OH or —NH2 or —NPhth; phenyl group optionally substituted with halogen, amino, nitro, C1-C6 alkyl; R (in the base) is selected from H, C1-C4 alkyl, halogen; Q=H with the proviso that C—N double bond is absent, C—Z double bond is present and Z is O; Z is NH$_2$ with the proviso that C—Z double bond is absent, Q≠H; Z is O with the proviso that C—N double bond is absent;

with the proviso that when both n=1 and m=1, A" is absent and A'" is selected from 1,3-dihydroisobenzofuran of formula (1a) or isochroman [3,4-dihydro-1H-benzo[c]pyran] represented by the formula (1b), A and A' are selected from H, lower alkyl, —OH, —OAc, —CH$_2$OH, —CH$_2$OAc; R, R' and R" in 1,3-dihydroisobenzofuran of formula (1a) or isochroman [3,4-dihydro-1H-benzo[c]pyran] represented by the formula (1b) are selected from H, —OH, —OAc, halo group, —CH2OH, —CH2OAc, —COOH, —COOMe, C1-C30 straight or branched alkyl group, optionally substituted with halogen or —OH or —NH2 or —NPhth; phenyl group optionally substituted with halogen, amino, nitro, C1-C6 alkyl; R (in the base) is selected from H, C1-C4 alkyl, halogen; Q=H with the proviso that C—N double bond is absent, C—Z double bond is present and Z is O; Z is NH$_2$ with the proviso that C—Z double bond is absent, Q≠H; Z is O with the proviso that C—N double bond is absent;

with the proviso that both A and A" can form together 1,3-dihydroisobenzofuran (1a) where R, R' and R", are selected from H, —OH, halo group, —CH$_2$OH, —CH$_2$OAc, —COOH, —COOMe, C1-C30 straight or branched alkyl group, optionally substituted with halogen or —OH or —NH$_2$ or —NPhth; phenyl group optionally substituted with halogen, amino, nitro, C1-C6 alkyl when m=0[i.e (CH2)m=0], A'" is absent and A' is selected from H, lower alkyl, —OH, —OAc, —CH$_2$OH, —CH$_2$OAc, —CH$_2$OMe, —CH$_2$OEt, phenyl optionally substituted with halogen, amino, nitro, C1-C6 alkyl.

In an aspect, a library of spiro annulated nucleosides is obtained by modification on the sugar moiety of the nucleoside by [2+2+2]-cyclotrimerization of the penultimate nucleoside diyne with symmetrical and unsymmetrical alkyne in presence of Rh or Ru complex catalyst in good yield.

In an embodiment of the present invention the Spiro annulated nucleoside of general formula I, wherein the structural formulae of the representative compounds are

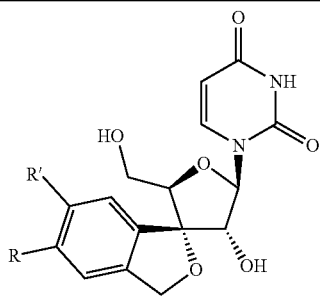

18 R = R' = H
24 R = R' = CH$_2$OAc
30 R or R' = C$_5$H$_{11}$

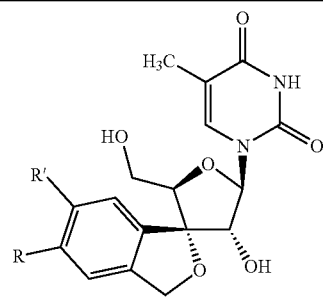

19 R = R' = H
25 R = R' = CH$_2$OAc
31 R or R' = C$_5$H$_{11}$

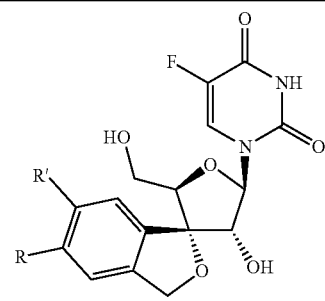

20 R = R' = H
26 R = R' = CH$_2$OAc
32 R or R' = C$_5$H$_{11}$

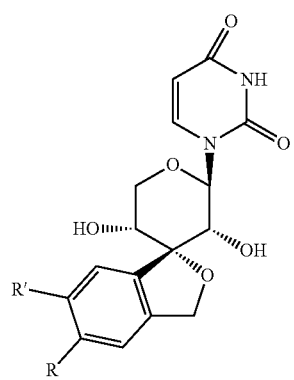

21 R = R' = H
27 R = R' = CH$_2$OAc
33 R or R' = C$_5$H$_{11}$

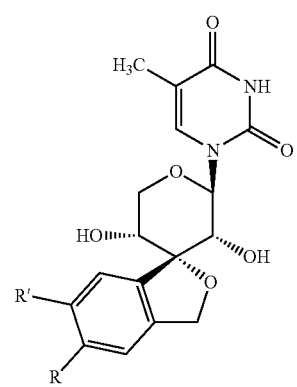

22 R = R' = H
28 R = R '= CH$_2$OAc
34 R or R' = C$_5$H$_{11}$

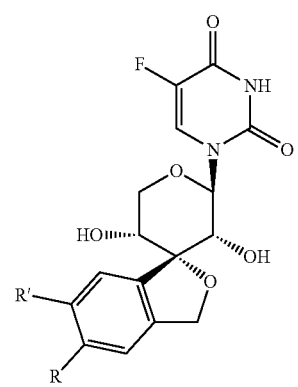

23 R = R' = H
29 R = R' = CH$_2$OAc
35 R or R' = C$_5$H$_{11}$

-continued

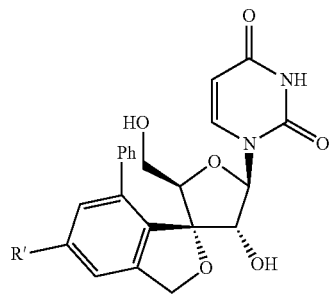

54 R' = —Ph
55 R' = —$^nC_6H_{13}$
56 R' = —$^nC_{21}H_{43}$
57 R' = —(CH$_2$)$_3$Cl
58 R' = —CH$_2$NPht
59 R' = m-(Ar—NH$_2$)

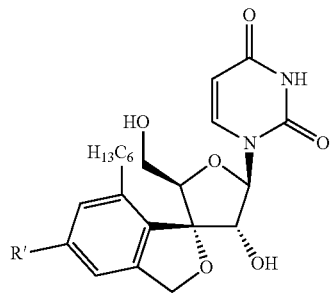

60 R' = —Ph
61 R' = —$^nC_6H_{13}$
62 R' = —$^nC_{21}H_{43}$
63 R' = —(CH$_2$)$_3$Cl

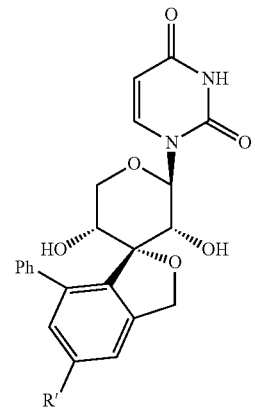

64 R' = —Ph (dr = 7:1)
65 R' = —$^nC_6H_{13}$
66 R' = —$^nC_{21}H_{43}$
67 R' = —(CH$_2$)$_3$Cl

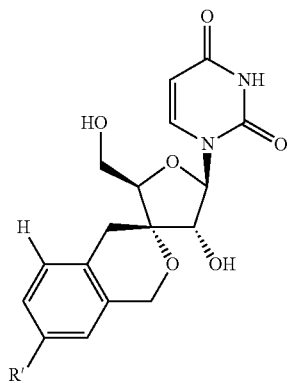

78 R' = H
79 R' = —Ph
80 R' = —$^nC_6H_{13}$
81 R' = —$^nC_{21}H_{43}$
82 R' = —(CH$_2$)$_3$Cl
83 R' = —CH$_2$NPht
84 R' = m-(Ar—NH$_2$)

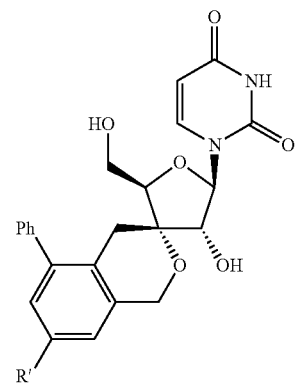

85 R' = H
86 R' = —Ph
87 R' = —$^nC_6H_{13}$
88 R' = —$^nC_{21}H_{43}$
89 R' = —(CH$_2$)$_3$Cl
90 R' = —CH$_2$NPht
91 R' = m-(Ar—NH$_2$)

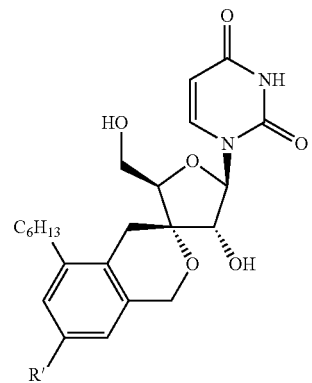

92 R' = H
93 R' = —Ph
94 R' = —$^nC_6H_{13}$
95 R' = —$^nC_{21}H_{43}$
96 R' = —(CH$_2$)$_3$Cl
97 R' = —CH$_2$NPht
98 R' = m-(Ar—NH$_2$)

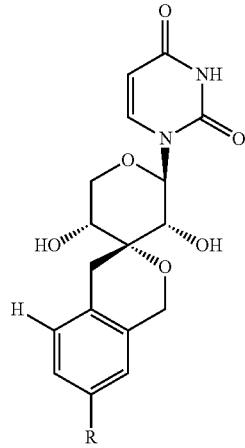

99 R' = H
100 R' = —Ph
101 R' = —$^nC_6H_{13}$
102 R' = —$^nC_{21}H_{43}$

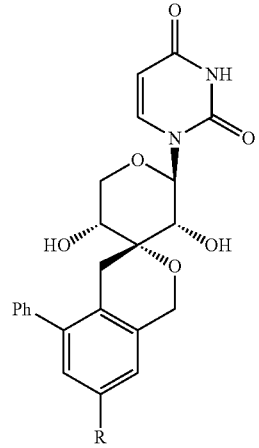

106 R' = H
107 R' = —Ph
108 R' = —$^nC_6H_{13}$
109 R' = —$^nC_{21}H_{43}$

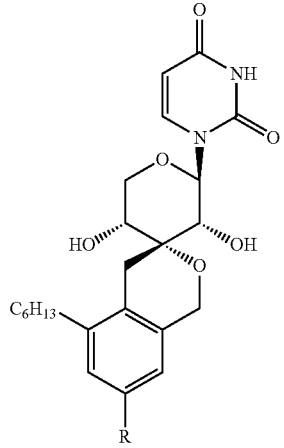

113 R' = H
114 R' = —Ph
115 R' = —$^nC_6H_{13}$
116 R' = —$^nC_{21}H_{43}$

-continued

| 103 R' = —(CH₂)₃Cl | 110 R' = —(CH₂)₃Cl | 117 R' = —(CH₂)₃Cl |
| 104 R' = —CH₂NPht | 111 R' = —CH₂NPht | 118 R' = —CH₂NPht |
| 105 R' = m-(Ar—NH₂) | 112 R' = m-(Ar—NH₂) | 119 R' = m-(Ar—NH₂) |

In another embodiment of the present invention the Spiro annulated nucleoside of general formula I is represented by the group of the following compounds 1-[3-C-Ethynyl-3-O-(2-propynyl)-β-D-ribo-pentofuranosyl]uracil (01):

1-[3-C-Ethynyl-3-O-(2-propynyl)-β-D-ribo-pentofuranosyl]thymine (02):

1-[3-C-Ethynyl-3-O-(2-propynyl)-β-D-ribo-pentofuranosyl]5-flurouracil (03):

1-[3-C-Ethynyl-3-O-(2-propynyl)-β-D-ribopyranosyl]uracil (04):

1-[3-C-Ethynyl-3-O-(2-propynyl)-β-D-ribopyranosyl]thymine (05):

1-[3-C-Ethynyl-3-O-(2-propynyl)-β-D-ribopyranosyl]5-flurouracil (06):

1-[3-C-Phenylethynyl-3-O-(2-propynyl)-β-D-ribo-pentofuranosyl]uracil (36):

1-[3-C-(1-Octynyl)-3-O-(2-propynyl)-β-D-ribo-pentofuranosyl]uracil (37):

1-[3-C-Phenylethynyl-3-O-(2-propynyl)-β-D-ribopyranosyl]uracil (38):

1-[3-C-Propynyl-3-O-(2-propynyl)-β-D-ribo-pentofuranosyl]uracil (74a):

1-[3-C-Phenylpropynyl-3-O-(2-propynyl)-β-D-ribo-pentofuranosyl]thymine (74b):

1-[3-C-″Hexyl propynyl-3-O-(2-propynyl)-β-D-ribo-pentofuranosyl]5-flurouracil (74c):

1-[3-C-Propynyl-3-O-(2-propynyl)-β-D-ribopyranosyl]uracil (77a):

1-[3-C-Phenylpropynyl-3-O-(2-propynyl-β-D-ribopyranosyl]thymine (77b):

1-[3-C-″Hexylpropynyl-3-O-(2-propynyl)-β-D-ribopyranosyl]5-flurouracil (77c):

1-[3-C,3-O-(o-Phenylenemethylene)-β-D-ribofuranosyl]uracil (18):

1-[3-C,3-O-(o-Phenylenemethylene)-β-D-ribofuranosyl]thymine (19):

1-[3-C,3-O-(o-Phenylenemethylene)-β-D-ribofuranosyl]5-flurouracil (20):

1-[3-C,3-O-(o-Phenylenemethylene)-β-D-ribopyranosyl]uracil (21):

1-[3-C,3-O-(o-Phenylenemethylene)-β-D-ribopyranosyl]thymine (22):

1-[3-C,3-O-(o-Phenylenemethylene)-β-D-ribopyranosyl]5-flurouracil (23):

1-[3-C,3-O-{o-(3,4-Di-acetyloxymethyl)-phenylenemethylene}-β-D-ribofuranosyl]uracil (24):

1-[3-C,3-O-{o-(3,4-Di-acetyloxymethyl-phenylenemethylene}-β-D-ribofuranosyl]thymine (25):

1-[3-C,3-O-{o-(3,4-Di-acetyloxymethyl)-phenylenemethylene}-β-D-ribofuranosyl]5-flurouracil (26):

1-[3-C,3-O-{o-(3,4-Di-acetyloxymethyl)-phenylenemethylene}-β-D-ribopyranosyl]uracil (27):

1-[3-C,3-O-{o-(3,4-Di-acetyloxymethyl)-phenylenemethylene}-β-D-ribopyranosyl]thymine (28):

1-[3-C,3-O-{o-(3,4-Di-acetyloxymethyl)-phenylenemethylene}-β-D-ribopyranosyl]5-flurouracil (29):

1-[3-C,3-O-{o-(3/4-″Pentyl)-phenylenemethylene}-β-D-ribofuranosyl]uracil (30):

1-[3-C,3-O-{o-(3/4-″Pentyl)-phenylenemethylene}-β-D-ribofuranosyl]thymine (31):

1-[3-C,3-O-{o-(3/4-″Pentyl)-phenylenemethylene}-β-D-ribofuranosyl]5-flurouracil (32):

1-[3-C,3-O-{o-(3/4-″Pentyl)-phenylenemethylene}-β-D-ribopyranosyl]uracil (33):

1-[3-C,3-O-{o-(3/4-″Pentyl)-phenylenemethylene}-β-D-ribopyranosyl]thymine (34):

1-[3-C,3-O-{o-(3/4-″Pentyl)-phenylenemethylene}-β-D-ribopyranosyl]5-flurouracil (35):

1-[3-C,3-O-{o-(2,4-Diphenyl)-phenylenemethylene}-β-D-ribofuranosyl]uracil (54):

1-[3-C,3-O-{o-(2-Phenyl-4-″hexyl)-phenylenemethylene}-β-D-ribofuranosyl]uracil (55):

1-[3-C,3-O-{o-(2-Phenyl-4-″henicosyl)-phenylenemethylene}-β-D-ribofuranosyl]uracil (56):

1-[3-C,3-O-{o-(2-Phenyl-4-chloropropyl)-phenylenemethylene}-β-D-ribofuranosyl]uracil (57):

1-[3-C,3-O-{o-(2-Phenyl-4-phthalimidomethyl)-phenylenemethylene}-β-D-ribofuranosyl]uracil (58):

1-[3-C,3-O-{o-(2-Phenyl-4-(3-aminophenyl))-phenylenemethylene}-β-D-ribofuranosyl]uracil (59):

1-[3-C,3-O-{o-(2-″Hexyl-4-phenyl)-phenylenemethylene}-β-D-ribofuranosyl]uracil (60):

1-[3-C,3-O-{o-(2-″Hexyl-4-″hexyl)-phenylenemethylene}-β-D-ribofuranosyl]uracil (61):

1-[3-C,3-O-{o-(2-″Hexyl-4-″henicosyl)-phenylenemethylene}-β-D-ribofuranosyl]uracil (62):

1-[3-C,3-O-{o-(2-″Hexyl-4-chloropropyl)-phenylenemethylene}-β-D-ribofuranosyl]uracil (63):

1-[3-C,3-O-{o-(2,4-Diphenyl)-phenylenemethylene}-β-D-ribopyranosyl]uracil (64)

1-[3-C,3-O-{o-(2-phenyl-4-″hexyl)-phenylenemethylene}-β-D-ribopyranosyl]uracil (65):

1-[3-C,3-O-{o-(2-phenyl-4-″henicosyl)-phenylenemethylene}-β-D-ribopyranosyl]uracil (66):

1-[3-C,3-O-{o-(2-phenyl-4-chloropropyl)-phenylenemethylene}-β-D-ribopyranosyl]uracil (67):

1-[3-C,3-O-{o-Benzylmethylene}-β-D-ribofuranosyl]uracil (78)

1-[3-C,3-O-{o-(5-Phenyl)-Benzylmethylene}-β-D-ribofuranosyl]uracil (79)

1-[3-C,3-O-{o-(5-″Hexyl)-Benzylmethylene}-β-D-ribofuranosyl]uracil (80)

1-[3-C,3-O-{o-(5-″henicosyl)-Benzylmethylene}-β-D-ribofuranosyl]uracil (81)

1-[3-C,3-O-{o-(5-chloropropyl)-Benzylmethylene}-β-D-ribofuranosyl]uracil (82)

1-[3-C,3-O-{o-(5-phthalimidomethyl)-Benzylmethylene}-β-D-ribofuranosyl]uracil (83)

1-[3-C,3-O-{o-[5-(3-aminophenyl)]-Benzylmethylene}-β-D-ribofuranosyl]uracil (84)

1-[3-C,3-O-{o-(3-Phenyl)-Benzylmethylene}-β-D-ribofuranosyl]uracil (85)

1-[3-C,3-O-{o-(3-Phenyl-5-Phenyl)-Benzylmethylene}-β-D-ribofuranosyl]uracil (86)

1-[3-C,3-O-{o-(3-Phenyl-5-″Hexyl)-Benzylmethylene}-β-D-ribofuranosyl]uracil (87)

1-[3-C,3-O-{o-(3-Phenyl-5-″henicosyl)-Benzylmethylene}-β-D-ribofuranosyl]uracil (88)

1-[3-C,3-O-{o-(3-Phenyl-5-chloropropyl)-Benzylmethylene}-β-D-ribofuranosyl]uracil (89)
1-[3-C,3-O-{o-(3-Phenyl-5-phthalimidomethyl)-Benzylmethylene}-β-D-ribofuranosyl]uracil (90)
1-[3-C,3-O-{o-[3-Phenyl-5-(3-aminophenyl)]-Benzylmethylene}-β-D-ribofuranosyl]uracil (91)
1-[3-C,3-O-{o-(3-"Hexyl)-Benzylmethylene}-β-D-ribofuranosyl]uracil (92)
1-[3-C,3-O-{o-(3-"Hexyl-5-Phenyl)-Benzylmethylene}-β-D-ribofuranosyl]uracil (93)
1-[3-C,3-O-{o-(3-"Hexyl-5-"Hexyl)-Benzylmethylene}-β-D-ribofuranosyl]uracil (94)
1-[3-C,3-O-{o-(3-"Hexyl-5-"henicosyl)-Benzylmethylene}-β-D-ribofuranosyl]uracil (95)
1-[3-C,3-O-{o-(3-"Hexyl-5-chloropropyl)-Benzylmethylene}-β-D-ribofuranosyl]uracil (96)
1-[3-C,3-O-{o-(3-"Hexyl-5-phthalimidomethyl)-Benzylmethylene}-β-D-ribofuranosyl]uracil (97)
1-[3-C,3-O-{o-[3-"Hexyl-5-(3-aminophenyl)]-Benzylmethylene}-β-D-ribofuranosyl]uracil (98)
1-[3-C,3-O-{o-Benzylmethylene}-β-D-ribopyranosyl]uracil (99)
1-[3-C,3-O-{o-(5-Phenyl)-Benzylmethylene}-β-D-ribopyranosyl]uracil (100)
1-[3-C,3-O-{o-(5-"Hexyl)-Benzylmethylene}-β-D-ribopyranosyl]uracil (101)
1-[3-C,3-O-{o-(5-"henicosyl)-Benzylmethylene}-β-D-ribopyranosyl]uracil (102)
1-[3-C,3-O-{o-(5-chloropropyl)-Benzylmethylene}-β-D-ribopyranosyl]uracil (103)
1-[3-C,3-O-{o-(5-phthalimidomethyl)-Benzylmethylene}-β-D-ribopyranosyl]uracil (104)
1-[3-C,3-O-{o-[5-(3-aminophenyl)]-Benzylmethylene}-β-D-ribopyranosyl]uracil (105)
1-[3-C,3-O-{o-(3-Phenyl)-Benzylmethylene}-β-D-ribopyranosyl]uracil (106)
1-[3-C,3-O-{o-(3-Phenyl-5-Phenyl)-Benzylmethylene}-β-D-ribopyranosyl]uracil (107)
1-[3-C,3-O-{o-(3-Phenyl-5-"Hexyl)-Benzylmethylene}-β-D-ribopyranosyl]uracil (108)
1-[3-C,3-O-{o-(3-Phenyl-5-"henicosyl)-Benzylmethylene}-β-D-ribopyranosyl]uracil (109)
1-[3-C,3-O-{o-(3-Phenyl-5-chloropropyl)-Benzylmethylene}-β-D-ribopyranosyl]uracil (110)
1-[3-C,3-O-{o-(3-Phenyl-5-phthalimidomethyl)-Benzylmethylene}-β-D-ribopyranosyl]uracil (111)
1-[3-C,3-O-{o-[3-Phenyl-5-(3-aminophenyl)]-Benzylmethylene}-β-D-ribopyranosyl]uracil (112)
1-[3-C,3-O-{o-(3-"Hexyl)-Benzylmethylene}-β-D-ribopyranosyl]uracil (113)
1-[3-C,3-O-{o-(3-"Hexyl-5-Phenyl)-Benzylmethylene}-β-D-ribopyranosyl]uracil (114)
1-[3-C,3-O-{o-(3-"Hexyl-5-"Hexyl)-Benzylmethylene}-β-D-ribopyranosyl]uracil (115)
1-[3-C,3-O-{o-(3-"Hexyl-5-"henicosyl)-Benzylmethylene}-β-D-ribopyranosyl]uracil (116)
1-[3-C,3-O-{o-(3-"Hexyl-5-chloropropyl)-Benzylmethylene}-β-D-ribopyranosyl]uracil (117)
1-[3-C,3-O-{o-(3-"Hexyl-5-phthalimidomethyl)-Benzylmethylene}-β-D-ribopyranosyl]uracil (118)
1-[3-C,3-O-{o-[3-"Hexyl-5-(3-aminophenyl)]-Benzylmethylene}-β-D-ribopyranosyl]uracil (119)

In another embodiment of the present invention the Spiro annulated nucleoside of general Formula I is useful as potential anti-cancer and anti-viral agents.

In another embodiment of the present invention a process for the preparation of Spiro annulated nucleoside of general Formula I, wherein the said process comprising the steps of;
a) preparing solution of diyne and alkyne in mole ratio ranging between 1:1 to 1:3 in a solvent followed by degassing of solution with dry argon;
b) adding a catalyst in mole ratio ranging between 0.02 to 0.05 into the degassed solution as obtained in step (a) followed by heating at temperature in the range of 70° C.-90° C. for a period in the range of 6 h-12 h;
c) cooling the solution as obtained in step (b) to room temperature ranging between 25° C.-30° C. followed by solvent evaporation and purification to obtain spiroannulated nucleoside.

In another embodiment of the present invention a process for the preparation of Spiro annulated nucleoside of general Formula I, wherein the said process comprising the steps of;
a. charging of diyne in a solvent in a sealed tube followed by degassing with alkyne;
b. adding a catalyst into the solution as obtained in step (a);
c. cooling the reaction mixture as obtained in step (b) at temperature ranging between −80° C.--70° C. followed by bubbling of alkyne for a period ranging between 25 min. to 60 min and sealing of tube;
d. transferring the sealed tube as obtained in step (c) in a steal bomb and heating at temperature ranging between 70° C.-90° C. for a period ranging between 6 h-12 h followed by cooling to room temperature ranging between 25° C.-30° C.;
e. evaporating the solvent from reaction mixture as obtained in step (d) and purification to obtain spiroannulated nucleoside.

In another embodiment of the present invention a process, wherein penultimate nucleoside diynes used in step (a) is selected from the group consisting of furanoside nucleoside, pyranoside nucleoside (1-[3-C-phenylethynyl-3-O-(2-propynyl)-β-D-ribo-pentofuranosyl]uracil), (1-[3-C-(1-octynyl)-3-O-(2-propynyl)-β-D-ribo-pentofuranosyl]uracil), (1[3-C-phenylethynyl-3-O-(2-propynyl)-β-D-ribopyranosyl]uracil), 1-[3-C-Propynyl/Phenylpropynyl/"Hexylpropynyl-3-O-(2-propynyl)-β-D-ribo-pentofuranosyl]5-flurouracil), (1[3-C-Propynyl/Phenylpropynyl/"Hexylpropynyl-3-O-(2-propynyl)-β-D-ribopyranosyl]5-flurouracil).

In another embodiment of the present invention a process, wherein the symmetrical and unsymmetrical alkynes used in step (a) and also in step (c) is selected from the group consisting of acetylene (CH≡CH), terminal alkyne of the formula R—C≡CH where R is selected from C1-C30 straight or branched alkyl groups optionally substituted with halo, —OH, —OAc, —CH$_2$OH; a phenyl group further optionally substituted with lower alkyl, halo, —OH, —OAc; diacetate of 2-butyne-1,4-diol, an alkyne of the formula R"—C≡C—R''' where R" and R''' are selected from either straight or branched chain alkyl group, —CH$_2$OH, —CH$_2$OAc, —COOH, —COOAc, TMS,N-propyne pthalimide.

In another embodiment of the present invention 1,3-dihydroisobenzofuran is appended on the sugar moiety of the nucleoside via [2+2+2] cyclotrimerization reaction.

In another embodiment of the present invention isochroman [3,4-dihydro-1H-benzo[c]pyran] is appended on the sugar moiety of the nucleoside via [2+2+2] cyclotrimerization reaction.

In another embodiment of the present invention the spiroannulation of the nucleoside diyne with the symmetrical and unsymmetrical alkyne takes place at C-3 of the furanoside ring.

In another embodiment of the present invention the spiroannulation of the nucleoside diyne with the symmetrical and unsymmetrical alkyne takes place at C-3 of the pyranoside ring.

In another embodiment of the present invention catalyst used in step (b) is selected from Wilkinson's catalyst [RhCl(PPh3)3, Cp*RuCl(cod) and [Rh(cod)2]BF4/(R)-BINAP.

In another embodiment of the present invention solvent used in step (a) is selected from the group consisting of toluene, xylene, methanol, ethanol, propanols and mixture thereof.

In another embodiment of the present invention yield of spiroannulated nucleoside is in the range of 71-87%.

DETAILED DESCRIPTION

Figure 1:
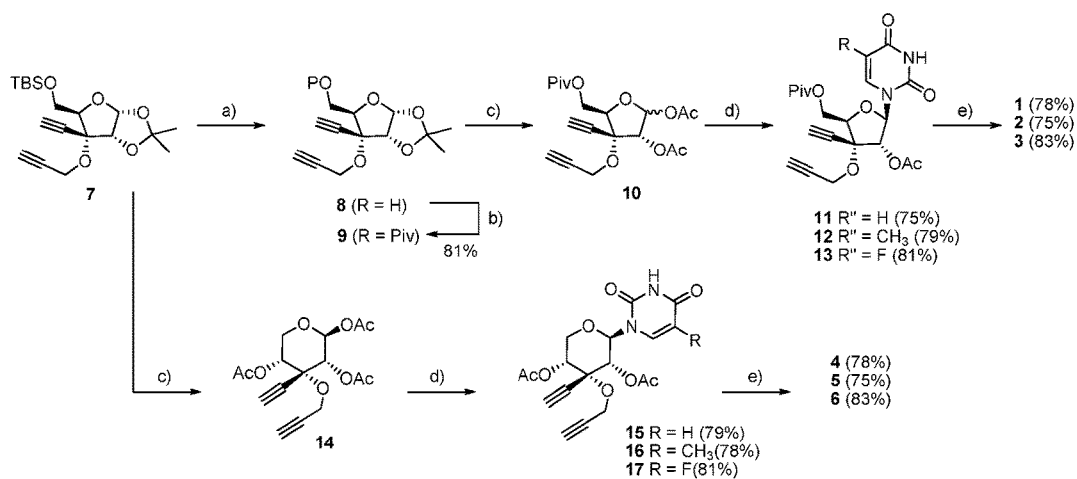
FIG. 1. Reagents and Conditions: a) TBAF, THF, rt, 8 h; b) PivCl, DMAP, CH$_2$Cl$_2$, rt, 6 h; c) i. 60% AcOH. reflux, 2 h; ii. Ac$_2$O, Et$_3$N, DMAP, CH$_2$Cl$_2$, rt, 1 h; d) uracil/5-flurouracil/thymine N,O-bis(trimethylsilyl)-acetamide (BSA), TMSOTf, CH$_3$CN, 50° C., 2 h; e) NaOMe, MeOH, rt, 20 min.
Figure 2:
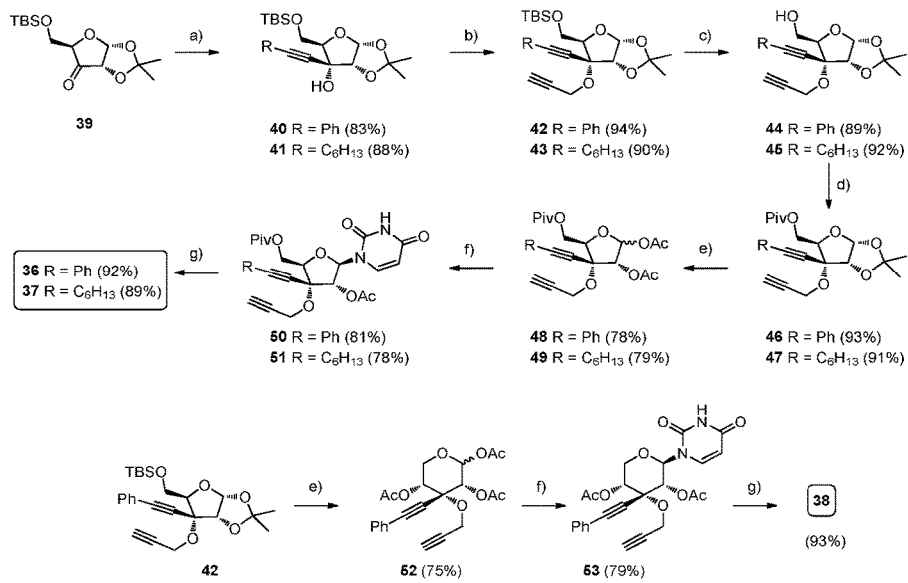
FIG. 2: Reagents and Conditions: a) n-BuMgCl, phenyl acetylene/1-octyne, 0° C. 1 h; b) NaH, THF. 0° C.—rt, 3 h; c) TBAF, THF, rt, 8 h; d) PivCl, DMAP, CH$_2$Cl$_2$, 0° C.—rt, 6 h; e) i. 60% AcOH, reflux, 2 h; ii. Ac$_2$O, Et$_3$N, DMAP, CH$_2$Cl$_2$, rt, 1 h; 1) uracil/5-flurouracil/thymine N,O-bis (trimethylsilyl)-acetamide (BSA), TMSOTf, CH$_3$CN, 50° C., 2 h; g) NaOMe. MeOH, rt, 20 min.
Figure 3:
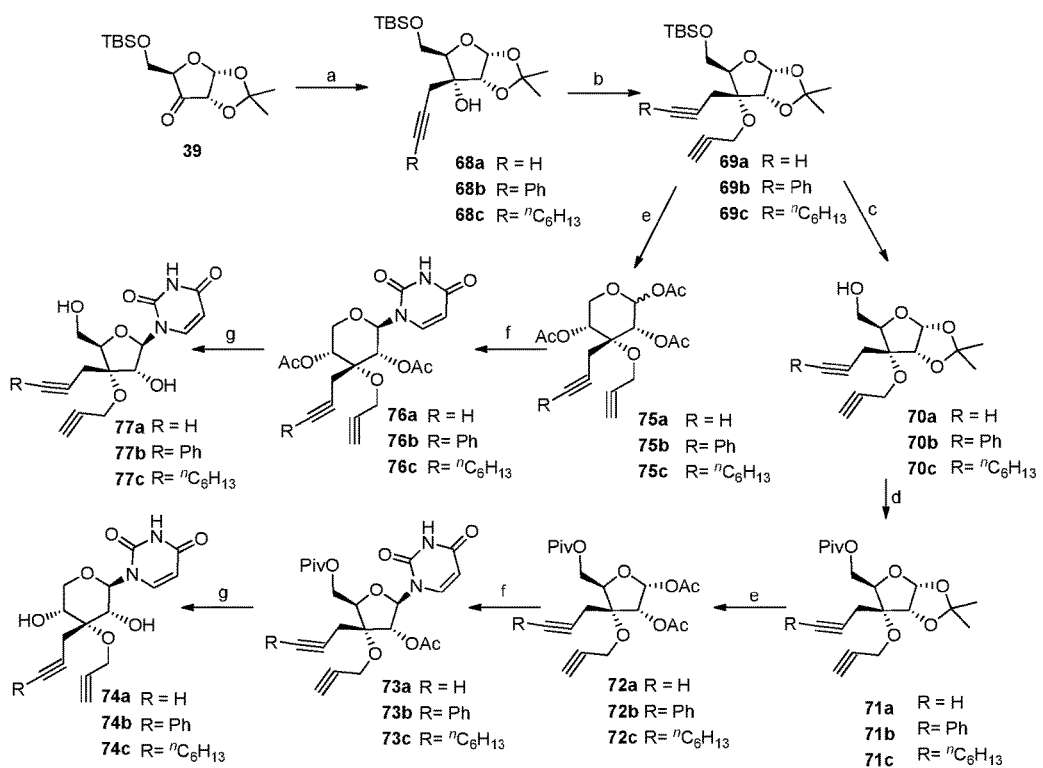
FIG. 3: Reagents and Conditions: a) Zn, Propargyl/substituted propargyl bromide, 0° C. 1 h; b) NaH, THF, 0° C.—rt, 3 h; c) TBAF, THF, rt, 8 h; d) PivCl, DMAP, CH$_2$Cl$_2$, 0° C.—rt, 6 h; e) i. 60% AcOH, reflux, 2 h; ii. Ac$_2$O, Et$_3$N, DMAP, CH$_2$Cl$_2$, rt, 1 h; f) uracil,N,O-bis(trimethylsilyl)-acetamide (BSA). TMSOTf (trimethylsilyl trifluoromethanesulphonate), CH$_3$CN, 50° C., 2 h; g) NaOMe, MeOH, rt, 20 min.

The invention will now be described in detail in connection with certain preferred and optional embodiments, so that various aspects thereof may be more fully understood and appreciated and briefly described as follows:

The term "nucleoside" used herein refers to glycosylamines consisting of a nucleobase (often referred to as simply base) bound to a ribose or deoxyribose sugar via a beta-glycosidic linkage.

The term "[2+2+2]-cyclotrimerization" or "cyclotrimerization" or "spiroannulation" extensively refer in the specification to intermolecular cycloaddition reaction between the penultimate nucleoside diynes with various symmetrical or unsymmetrical alkynes.

The present invention describes modification of the sugar backbone in the nucleoside for developing a library of small molecules that may control genetic disorders or infections.

Considering the fact that the benzenoid unit is ubiquitous in natural products as well as in medicinal compounds, it is foreseen that through judicious retrosynthetic planning and employing [2+2+2]-cyclotrimerisation, a rapid access to a collection of spiroannulated nucleosides can be made possible. Further, considering the prevalence of the isochroman or dihydroisobenzofuran structural unit in many of the naturally occurring substances, and drug candidates, the present invention provides a process, wherein, the said structural units are appended on the sugar template of the nucleoside by employing alkyne cyclotrimerisation.

Thus in an embodiment, the present invention discloses the synthesis of enantiopure tricyclic systems comprising of isochroman or dihydroisobenzofuran units integrated with sugar templates. The bicyclic ring construction on the sugar moiety in the nucleoside is effected via intermolecular [2+2+2] alkyne cyclotrimerization reaction of nucleoside diynes at the final stage thereby providing a provision to alter the functional groups on the newly formed aromatic rings. By selecting the representative diyne products, various tricyclic nucleosides are synthesized by simple synthetic manipulations.

The process of the present invention comprises intermolecular [2+2+2] cyclotrimerization reaction of symmetrical or unsymmetrical alkynes with the nucleoside diynes to obtain enantiopure tricyclic systems of the general Formula I;

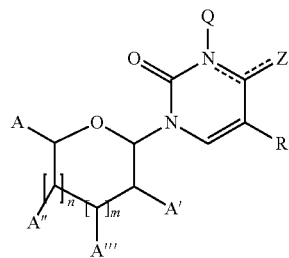

where, R (in the base) is selected from H, C$_1$-C$_4$ alkyl, halogen, OR, NHR (R=H, COCH$_3$, COO$^t$Bu); Q=H with the proviso that C—N double bond is absent, C—Z double bond is present and Z is O; Z is NH$_2$ with the proviso that C—Z double bond is absent, Q≠H; Z is O with the proviso that C—N double bond is absent;

A and A' are selected from H, lower alkyl, —OH, —OAc CH$_2$OH, —CH$_2$OAc, —CH$_2$OPiv, —CH$_2$OTBS; m and n are integers 0,1

A" and A''' are selected from 1,3-dihydroisobenzofuran (1a) or isochroman [3,4-dihydro-1H-benzo[c]pyran] represented by the formula (1b),

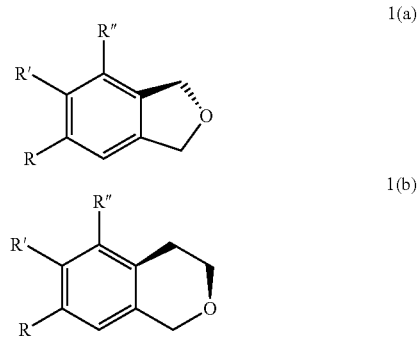

where R, R', R" are selected from H, —OH, halo group, —CH$_2$OH, —CH$_2$OAc, —COOH, —COOMe, C1-C30 straight or branched alkyl group, optionally substituted with halogen or —OH or —NH$_2$ or —NPhth; phenyl group optionally substituted with halogen, amino, nitro, C1-C6 alkyl;

with the proviso that when n=1[i.e(CH$_2$)n=1] and where m=0[i.e(CH$_2$)m=0], A''' is absent and A" is 1,3-dihydro isobenzofuran (1a) or isochroman [3,4-dihydro-1H-benzo[c]

pyran] represented by the formula (1b), directly annulated at C-3, A and A' are selected from H, lower alkyl, —OH, —OAc, —CH₂OH—CH₂OAc, —CH₂OPiv, —CH₂OTBS; and R, R' and R" in 1,3-dihydro isobenzofuran (1a) or isochroman [3,4-dihydro-1H-benzo[c]pyran] represented by the formula (1b) are selected from H, —OH, halo group, —CH₂OH, —CH₂OAc, —COOH, —COOMe, C1-C30 straight or branched alkyl group, optionally substituted with halogen or —OH or —NH₂ or —NPhth; phenyl group optionally substituted with halogen, amino, nitro, C1-C6 alkyl; R (in the base) is selected from H, C1-C4 alkyl, halogen; Q=H with the proviso that C—N double bond (....) is absent, C—Z double bond is present and Z is O; Z is NH₂ with the proviso that C—Z double bond is absent, Q≠H; Z is O with the proviso that C—N double bond is absent;

with the proviso that when both n=1 and m=1, A" is absent and A'" is selected from 1,3-dihydroisobenzofuran of formula (1a) or isochroman [3,4-dihydro-1H-benzo[c] pyran] represented by the formula (1b), A and A' are selected from H, lower alkyl, —OH, —OAc, —CH₂OH, —CH₂OAc; R, R' and R" in 1,3-dihydroisobenzofuran of formula (1a) or isochroman [3,4-dihydro-1H-benzo[c] pyran] represented by the formula (1b) are selected from H, —OH, —OAc, halo group, —CH₂OH, —CH₂OAc, —COOH, —COOMe, C1-C30 straight or branched alkyl group, optionally substituted with halogen or —OH or —NH₂ or —NPhth; phenyl group optionally substituted with halogen, amino, nitro, C1-C6 alkyl; R (in the base) is selected from H, C1-C4 alkyl, halogen; Q=H with the proviso that C—N double bond is absent, C—Z double bond is present and Z is O; Z is NH₂ with the proviso that C—Z double bond is absent, Q≠H; Z is O with the proviso that C—N double bond is absent;

with the proviso that both A and A" can form together 1,3-dihydroisobenzofuran (1a) where R, R' and R", are selected from H, —OH, halo group, —CH₂OH, —CH₂OAc, —COOH, —COOMe, C1-C30 straight or branched alkyl group, optionally substituted with halogen or —OH or —NH₂ or —NPhth; phenyl group optionally substituted with halogen, amino, nitro, C1-C6 alkyl when m=0[i.e(CH₂) m=0], A'" is absent and A' is selected from H, lower alkyl, —OH, —OAc, —CH₂OH, —CH₂OAc, —CH₂OMe, —CH₂OEt, phenyl optionally substituted with halogen, amino, nitro, C1-C6 alkyl.

The symmetrical and unsymmetrical alkynes are selected from the group comprising of acetylene (CH≡CH), terminal alkyne of the formula R—C≡CH where R is selected from C1-C30 straight or branched alkyl groups optionally substituted with halo, —OH, —OAc, —CH₂OH; a phenyl group further optionally substituted with lower alkyl, halo, —OH, —OAc; diacetate of 2-butyne-1,4-diol, an alkyne of the formula R"'—C≡C—R'" where R" and R'" are selected from either straight or branched chain alkyl group, —CH₂OH, —CH₂OAc, —COOH, —COOAc, TMS,N-propyne pthalimide.

In a preferred embodiment, the present invention discloses spiroannulation on the sugar template of the penultimate nucleoside diyne with various symmetrical and unsymmetrical alkynes.

Accordingly, in one of the preferred embodiment, the process of the present invention comprises intermolecular [2+2+2]-cyclotrimerization of the furanoside diyne 1-3, as suitable precursors with symmetrical and unsymmetrical alkynes in the presence of Wilkinson's catalyst [RhCl (PPh₃)₃].

In another preferred embodiment, the process of the present invention comprises intermolecular [2+2+2] cyclotrimerization of the pyranosidediyne 4-6, as suitable precursors with symmetrical and unsymmetrical alkynes in the presence of Wilkinson's catalyst [RhCl(PPh₃)₃].

The key furanoside and pyranoside diynes 1-6 employed in the present invention, wherein the critical spiroannulation is executed at the final stage, are synthesized from the known intermediate 7.

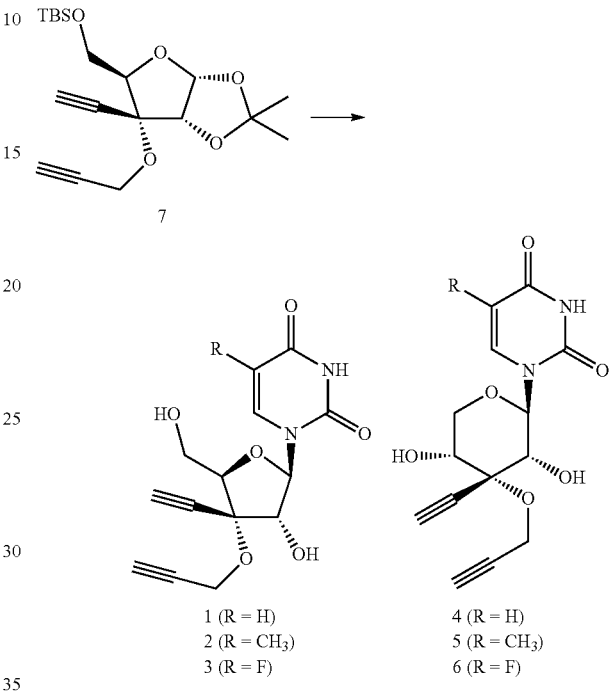

1-[3-C-Ethynyl-3-O-(2-propynyl)-β-D-ribo-pentofuranosyl]uracil (01):
1-[3-C-Ethynyl-3-O-(2-propynyl)-β-D-ribo-pentofuranosyl]thymine (02):
1-[3-C-Ethynyl-3-O-(2-propynyl)-β-D-ribo-pentofuranosyl]5-flurouracil (03):
1[3-C-Ethynyl-3-O-(2-propynyl)-β-D-ribopyranosyl]uracil (04):
1[3-C-Ethynyl-3-O-(2-propynyl)-β-D-ribopyranosyl]thymine (05):
1[3-C-Ethynyl-3-O-(2-propynyl)-β-D-ribopyranosyl]5-flurouracil (06):

Accordingly, compound 7 is converted to the corresponding pivolate derivative 9 by deprotection of the TBS ether using TBAF in THF and reprotection of the resulting alcohol 8 using pivoloyl chloride and Et₃N. Selective acetonide hydrolysis of compound 9 followed by acetylation (Ac₂O/ Et₃N) gave a 1:1 anomeric mixture of diacetates 10. The glycosidation of the anomeric mixture 10 is carried out under modified Vorbrüggen conditions employing uracil, thymine and 5-flurouracil preferably as glycosyl to afford the protected nucleosides 11-13, respectively. The protected nucleosides 11-13 are then subjected to Zemplen's deacetylation to yield furanose nucleosides 1-3, which have the key diyne unit for the cycloisomerization reactions.

Further, synthesis of the pyranosyl nucleoside precursors 4-6 involves initially deprotection of 9 using acetic acid followed by the peracetylation employing acetic anhydride and Et3N in dichloromethane to afford the corresponding β-anomer 14 exclusively. The N-glycosidation of 14 with pyrimidine base selected from uracil, 5-flurouracil and thymine under modified Vorbrüggen conditions followed by deacetylation of the resulting compounds 15-17 gave the pyranose nucleosides 4-6. The process for the synthesis of diynes 1-6 is schematically given in Scheme 1.

Thus according to the preferred embodiment, the furanoside diynes 1-3 and the pyranoside diyne 4-6 obtained above are subjected to trimerization with various symmetrical and unsymmetrical alkynes to obtain a library of small molecules of modified nucleosides.

The generalized reaction of the intermolecular [2+2+2]-cyclotrimerization of the nucleoside diynes 1-6 with various symmetrical or unsymmetrical alkynesis represented below:

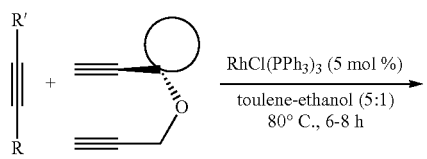

-continued

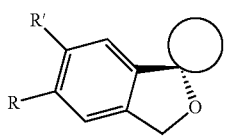

In an embodiment, the trimerization reaction of diynes 1-6 is carried out effectively with acetylene (R=R'=H) in presence of Wilkinson's catalyst in presence of solvent selected from aromatic hydrocarbons, lower alcohols at 80° C. in a sealed tube for 6-8 hours to obtain the corresponding products 18-23 respectively.

The aromatic hydrocarbons are selected from toluene, xylene, etc and the lower alcohols are selected from methanol, ethanol, propanols etc.

In another embodiment, the diynes 1-6 are reacted with the diacetate of 2-butyne-1,4-diol to obtain the corresponding isobenzofurannulated nucleosides 24-29 in good yields.

In yet another embodiment, the cyclotrimerization reactions of diynes 1-6 is carried out with 1-heptyne to yield the regiomeric mixtures 30-35.

The scope of the cyclotrimerisation reaction of diynes 1-6 is given below in Chart 1.

CHART 1

Scope of the cyclotrimerization reaction of diynes 1-6

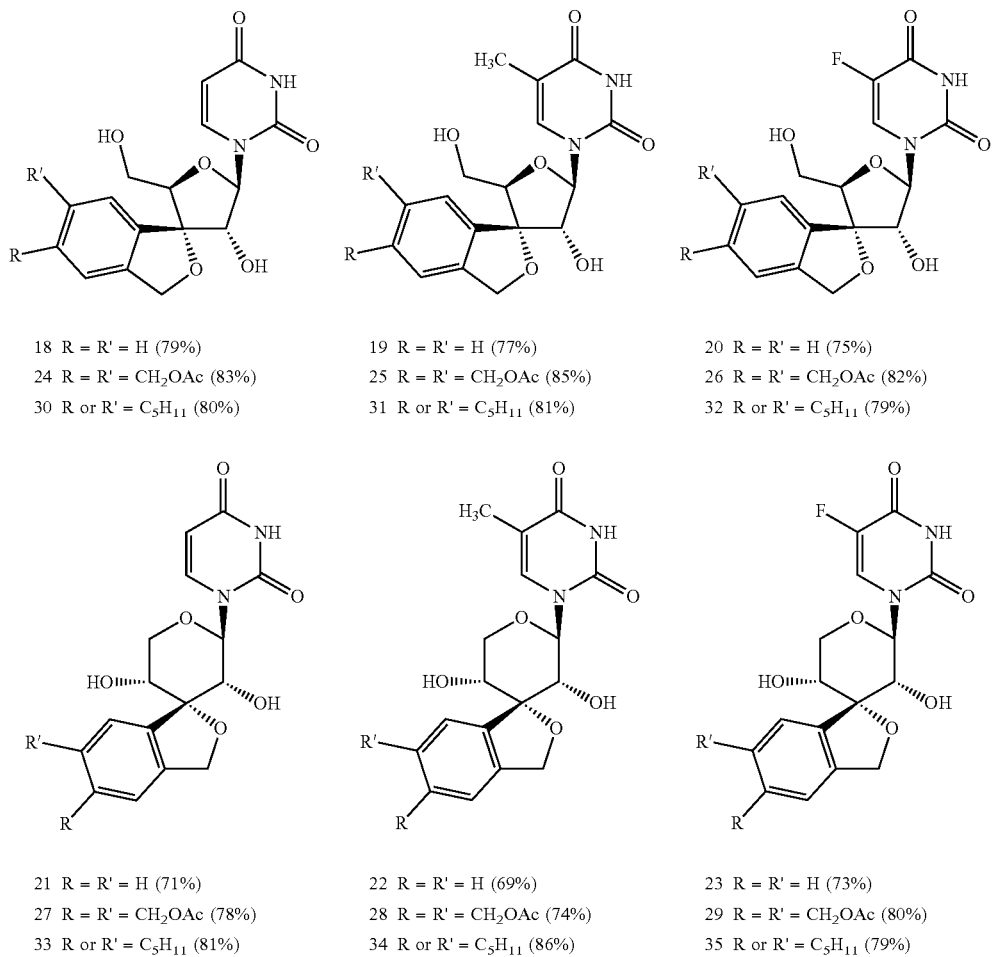

18 R = R' = H (79%)
24 R = R' = CH$_2$OAc (83%)
30 R or R' = C$_5$H$_{11}$ (80%)

19 R = R' = H (77%)
25 R = R' = CH$_2$OAc (85%)
31 R or R' = C$_5$H$_{11}$ (81%)

20 R = R' = H (75%)
26 R = R' = CH$_2$OAc (82%)
32 R or R' = C$_5$H$_{11}$ (79%)

21 R = R' = H (71%)
27 R = R' = CH$_2$OAc (78%)
33 R or R' = C$_5$H$_{11}$ (81%)

22 R = R' = H (69%)
28 R = R' = CH$_2$OAc (74%)
34 R or R' = C$_5$H$_{11}$ (86%)

23 R = R' = H (73%)
29 R = R' = CH$_2$OAc (80%)
35 R or R' = C$_5$H$_{11}$ (79%)

In another embodiment, cyclotrimerisation of diynes 1-6 with bis-(trimethylsilyl)acetylene and dimethyl acetylene dicarboxylate as representative symmetric disubstituted alkynes yielded, however, self-dimerized products or a complex mixture.

A similar lack of regioselectivity was observed when other catalysts such as Cp*RuCl(cod) and [Rh(cod)$_2$]BF$_4$/(R)-BINAP were employed.

The regioselectivity is the critical limitation with the [2+2+2]-cyclotrimerisation reactions, which has been addressed to some extent in the present invention by the placement of a substituent on any of the alkynes of the diyne unit.

In an embodiment of the present invention, cyclotrimerisation of diynes 36-38 with the terminal alkynes is carried out to determine the regioselectivity.

Accordingly, ketone 39 is reacted with alkynylmagnesium chloride (prepared by Grignard exchange between the corresponding alkyne and n-butylmagnesium chloride) followed by propargylation of 3°-hydroxyl in the resulting alkynols 40, 41 to obtain the diyne intermediates 42 and 43 respectively. The compounds 42 and 43 are then converted to the corresponding pivolate derivatives 46 and 47 followed by a sequence of TBS deprotection and pivoloylation reactions. Subsequent acetonide hydrolysis of 46 and 47, acetylation (Ac$_2$O/Et$_3$N) and the N-glycosidation with uracil, and final saponification under Zemplen's conditions yielded the furanose nucleosides 36 and 37. Further, deprotection of 42 using acetic acid followed by the peracetylation, N-glycosidation with uracil and deacetylation yielded pyranosyl nucleoside 38.

1-[3-C-Phenylethynyl-3-O-(2-propynyl)-β-D-ribo-pentofuranosyl]uracil (36):

1-[3-C-(1-Octynyl)-3-O-(2-propynyl)-β-D-ribo-pentofuranosyl]uracil (37):

1[3-C-Phenylethynyl-3-O-(2-propynyl)-β-D-ribopyranosyl]uracil (38):

Thus in another preferred embodiment, the furanoside diynes 36-37 and pyranoside diyne 38 are subjected to cyclotrimerisation reaction in presence of catalyst Cp*RuCl (cod) and in presence of DCE-ethanol (5:1) at room temperature yielded isobenzofurannulated products

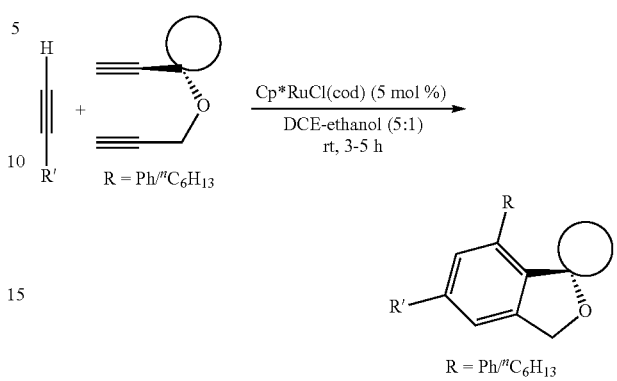

with excellent regioselectivity. The generalized reaction is given below:

Thus in an embodiment, cyclotrimerisation of diyne 36 (where R=Ph) with various terminal alkynes yielded compounds 54-59 in good yield and with excellent regioselectivity.

In another embodiment, cyclotrimerisation of diyne 37 (where R=C$_6$H$_{13}$) with various terminal alkynes yielded compounds 60-63 in good yield and with excellent regioselectivity.

In yet another embodiment, cyclotrimerisation of diyne 38 with phenyl acetylene gave a 7:1 regiomeric mixture, with the 1,3-product being the major one. The diynes 36 and 37 on reaction with phenyl acetylene yielded the 1,3-product exclusively.

The amine group present in the products 58, 59 and the chloro functional group present in the products and 57, 63, and 67 provide a suitable handle for further diversification in the present invention.

The scope of the cyclotrimerisation reaction of diynes 36-38 is given below in chart 2.

CHART 2

Scope of the cyclotrimerization reaction of diynes 36-38

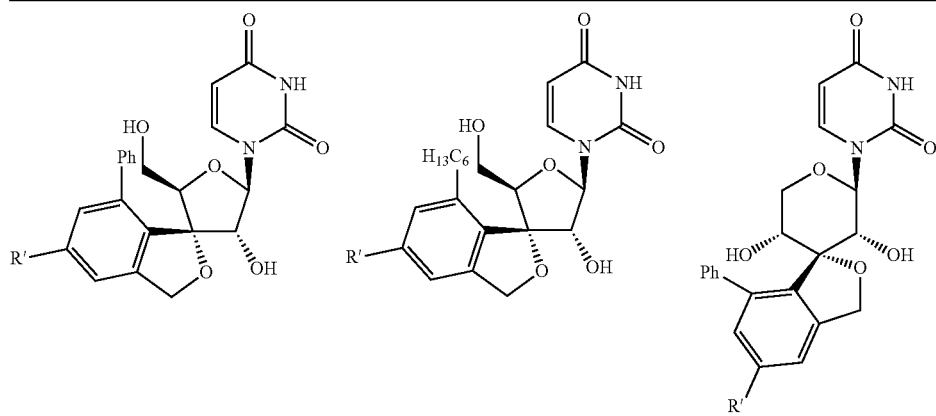

54 R' = —Ph (85%)
55 R' = —$^n$C$_6$H$_{13}$ (78%)
56 R' = —$^n$C$_{21}$H$_{43}$ (87%)
57 R' = —(CH$_2$)$_3$Cl (83%)
58 R' = —CH$_2$NPht (80%)
59 R' = m-(Ar—NH$_2$) (85%)

60 R' = —Ph (78%)
61 R' = —$^n$C$_6$H$_{13}$ (74%)
62 R' = —$^n$C$_{21}$H$_{43}$ (73%)
63 R' = —(CH$_2$)$_3$Cl (78%)

64 R' = —Ph (83%, dr = 7:1)
65 R' = —$^n$C$_6$H$_{13}$ (77%)
66 R' = —$^n$C$_{21}$H$_{43}$ (81%)
67 R' = —(CH$_2$)$_3$Cl (79%)

In yet another preferred embodiment, the present invention comprises the synthesis of Spiro-benzo-pyrannulated nucleosides. This includes converting ketone 39 to diyne intermediates as depicted in Scheme 3 below:

According to the Scheme 4, ketone 39 is converted to alkynols 68 by applying Barbier reaction with halo-alkyne e.g. propargyl bromide and substituted propargyl bromides (R=H, $C_6H_{13}$— and Ph-). Subsequent propargylation of 3°-hydroxyl in the resulting alkynols 68 gave the diyne intermediates 69. The preparation of furanoside diynes involved converting the intermediates 69 to the corresponding pivolate derivatives 71 following a sequence of TBS deprotection and pivoloylation reactions. Subsequent acetonide hydrolysis of 71, acetylation ($Ac_2O/Et_3N$) and the N-glycosidation with uracil, and final saponification under Zemplen's conditions afforded the furanose nucleosides 77. Synthesis of the pyranosyl nucleoside 74 includes the global deprotection of 69 using acetic acid followed by the per-acetylation, N-glycosidation with uracil and deacetylation.

In another preferred embodiment, the furanoside diyne 74 and pyranoside diyne 77 are subjected to [2+2+2]-cyclotrimerisation with various terminal diynes to obtain the desired spiroannulated nucleosides. The generalized spiroannulation is depicted below;

In an embodiment, the furanoside diyne 77a (R=H) is cyclotrimerized with various terminal alkynes (where R=H) to obtain the products 78-84 in good yields.

In another embodiment, the furanosidediyne 77b (R=Ph) is cyclotrimerized with various terminal alkynes (where R=H) to obtain the products 85-91 in good yields.

In yet another embodiment, the furanoside diyne 77c (R=$^nC_6H_{13}$) is cyclotrimerized with various terminal alkynes (where R=H) to obtain the products 92-98 in good yields.

In another embodiment, the pyranosidediyne 74a (R=H) is cyclotrimerized with various terminal alkynes (where R=H) to obtain the products 99-105 in good yields.

In yet another embodiment, the pyranoside diyne 74b (R=Ph) is cyclotrimerized with various terminal alkynes (where R=H) to obtain the products 106-112 in good yields.

In yet another embodiment, the pyranoside diyne 74c (R=$^nC_6H_{13}$) is cyclotrimerized with various terminal alkynes (where R=H) to obtain the products 113-119 in good yields.

1-[3-C-Propynyl-3-O-(2-propynyl)-β-D-ribo-pentofuranosyl]uracil (74a):

1-[3-C-Phenylpropynyl-3-O-(2-propynyl)-β-D-ribo-pentofuranosyl]thymine (74 b):

1-[3-C-$^n$Hexyl propynyl-3-O-(2-propynyl)-β-D-ribo-pentofuranosyl]5-flurouracil (74c):

1[3-C-Propynyl-3-O-(2-propynyl)-β-D-ribopyranosyl]uracil (77a):

1[3-C-Phenylpropynyl-3-O-(2-propynyl)-β-D-ribopyranosyl]thymine (77b):

1[3-C-$^n$Hexylpropynyl-3-O-(2-propynyl)-β-D-ribopyranosyl]5-flurouracil (77c):

The scope of cyclotrimerization of diynes 74 and 77 is given below in Chart 3

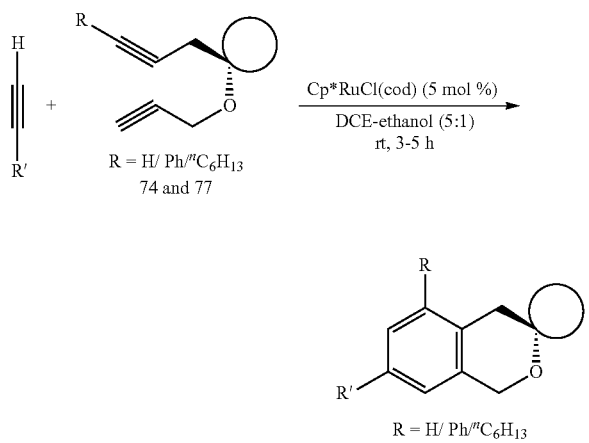

CHART 3

Scope of cyclotrimerization reaction of the diynes 74 and 77

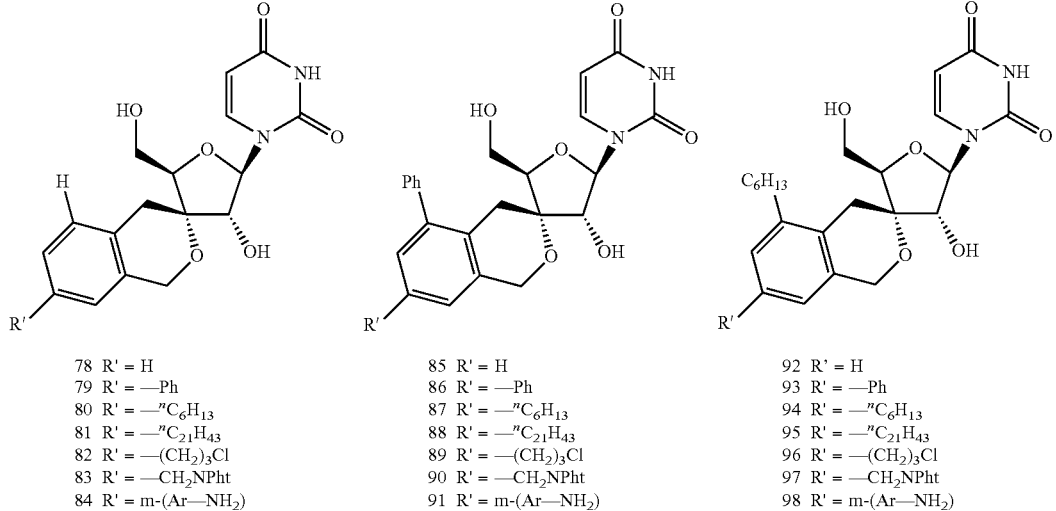

| 78 R' = H | 85 R' = H | 92 R' = H |
| 79 R' = —Ph | 86 R' = —Ph | 93 R' = —Ph |
| 80 R' = —$^nC_6H_{13}$ | 87 R' = —$^nC_6H_{13}$ | 94 R' = —$^nC_6H_{13}$ |
| 81 R' = —$^nC_{21}H_{43}$ | 88 R' = —$^nC_{21}H_{43}$ | 95 R' = —$^nC_{21}H_{43}$ |
| 82 R' = —$(CH_2)_3Cl$ | 89 R' = —$(CH_2)_3Cl$ | 96 R' = —$(CH_2)_3Cl$ |
| 83 R' = —$CH_2NPht$ | 90 R' = —$CH_2NPht$ | 97 R' = —$CH_2NPht$ |
| 84 R' = m-(Ar—$NH_2$) | 91 R' = m-(Ar—$NH_2$) | 98 R' = m-(Ar—$NH_2$) |

CHART 3-continued

Scope of cyclotrimerization reaction of the diynes 74 and 77

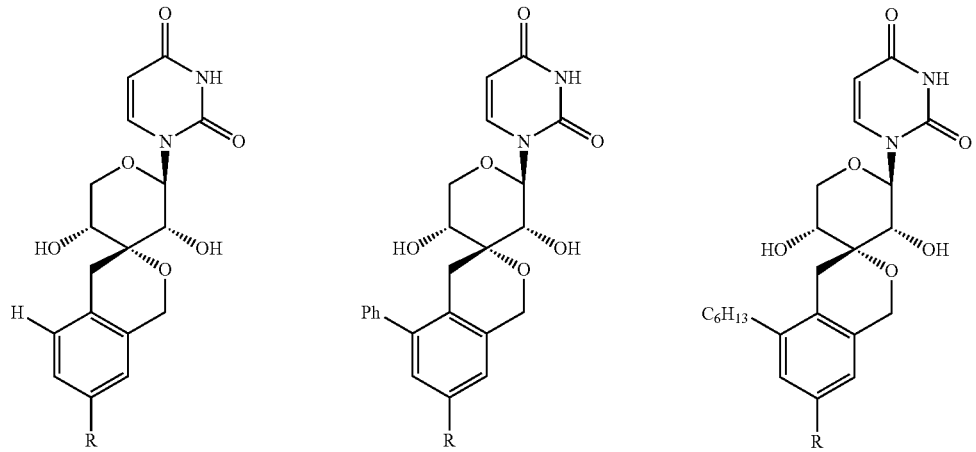

| 99 R' = H | 106 R' = H | 113 R' = H |
| 100 R' = —Ph | 107 R' = —Ph | 114 R' = —Ph |
| 101 R' = —"C$_6$H$_{13}$ | 108 R' = —"C$_6$H$_{13}$ | 115 R' = —"C$_6$H$_{13}$ |
| 102 R' = —"C$_{21}$H$_{43}$ | 109 R' = —"C$_{21}$H$_{43}$ | 116 R' = —"C$_{21}$H$_{43}$ |
| 103 R' = —(CH$_2$)$_3$Cl | 110 R' = —(CH$_2$)$_3$Cl | 117 R' = —(CH$_2$)$_3$Cl |
| 104 R' = —CH$_2$NPht | 111 R' = —CH$_2$NPht | 118 R' = —CH$_2$NPht |
| 105 R' = m-(Ar—NH$_2$) | 112 R' = m-(Ar—NH$_2$) | 119 R' = m-(Ar—NH$_2$) |

In an embodiment of the present invention, it is possible to develop a library of modified sugar template on the nucleoside by means of [2+2+2]-cyclotrimerisation as the last step of the process. Further, in the present invention by simple synthetic manipulations, D-xylose is modified into eleven different modified nucleosides having the diyne unit. The present strategy is further characterized by flexibility at the final stages and synthesis with a complete redox economy.

The present invention is illustrated herein below with examples, which are illustrative only and should not be construed to limit the scope of the present invention in any manner.

EXPERIMENTAL

General Methods: Air and/or moisture sensitive reactions were carried out in anhydrous solvents under an argon atmosphere in oven-dried glassware. All anhydrous solvents were distilled prior to use: Toluene from Na and benzophenone; CH$_2$Cl$_2$ and DMF from CaH$_2$; MeOH and EtOH from Mg cake. Commercial reagents were used without purification. Column chromatography was carried out by using Spectrochem silica gel (100-200 mesh). Optical rotations were determined on a Jasco DIP-370 digital polarimeter. Specific optical rotations $[\alpha]_D^{25}$ are given in $10^{-1}$ deg cm$^2$ g$^{-1}$. $^1$H and $^{13}$C NMR spectroscopy measurements were carried out on Bruker AC 200 MHz or Bruker DRX 400 MHz spectrometers, and TMS was used as internal standard. The $^1$H and $^{13}$C NMR chemical shifts are reported in ppm downfield from tetramethylsilane and the coupling constants (J) are reported in Hertz (Hz). The following abbreviations are used to designate signal multiplicity: s=singlet, d=doublet, t=triplet, q=quartet, m=multiplet, br=broad. The multiplicity of the $^{13}$C NMR signals was assigned with the help of DEPT spectra and the terms s=singlet, d=doublet, t=triplet and q=quartet represent C (quaternary), CH, CH$_2$ and CH$_3$ respectively. Mass spectroscopy was carried out on an API QStar Pulsar (Hybrid Quadrupole-TOF LC/MS/MS) spectrometer. Elemental analysis data were obtained on a Thermo Finnigan Flash EA 1112 Series CHNS Analyzer.

Representative Procedures for the [2+2+2]-Cyclotrimerization Reactions of Diynes:

Procedure A: A solution of diyne 1 (0.5 mmol) and alkyne (1.5 mmol) in 4:1 toluene/ethanol (12 mL) was degassed with dry argon for 20 min. To this, Wilkinson's catalyst [RhCl(PPh$_3$)$_3$] (0.03 mmol) was added, and the mixture was heated at 80° C. for 6 h and then allowed to cool to room temperature. The solvent evaporated under reduced pressure. The residue was purified by silica gel chromatography to procure the cyclotrimerization product.

Procedure B: A solution of diyne 1 (0.5 mmol) in toluene/ethanol (12 and 3 mL, respectively) in a sealed tube was degassed with dry alkyne for 20 min; then, Wilkinson's catalyst [RhCl(PPh$_3$)$_3$] (0.03 mmol) was introduced into the mixture. The reaction mixture was cooled to −78° C., and alkyne gas was condensed by continuous bubbling for 25 min. and the tube sealed by fusion. The sealed tube was transferred into steel bomb, heated at 80° C. for 6 h. After cooling to room temperature, the tube was broken and the mixture was transferred into a round-bottom flask and concentrated under reduced pressure. The residue was purified by silica gel chromatography (ethyl acetate in petroleum ether) to afford the cyclotrimerized product.

Procedure C: A solution of diyne 1 (0.5 mmol) and alkyne (0.5 mmol) in DCE (5 mL) was degassed with dry argon for 20 min. To this, Cp*RuCl(cod) catalyst (0.03 mmol) was added, and the mixture was stirred for 4-6 h at 25-30° C. The solvent evaporated under reduced pressure. The residue was purified by silica gel chromatography to procure the cyclotrimerization product.

EXAMPLES

Example 1

1-[3-C,3-O-(o-Phenylenemethylene)-β-D-ribofuranosyl] uracil (18): Following procedure B, using diyne 1 (100 mg, 0.33 mmol) and acetylene gas were used to get a product 18 (85.7 mg, 79% yield) as a White solid, mp: 234-236° C.; $[\alpha]_D^{25}$+14.3 (c 0.3, MeOH); IR (CHCl$_3$): 3630, 3371, 3018, 1728, 1522, 1421, 1375, 1216, 1120, 1048, 975, 757 cm$^{-1}$; $^1$H NMR (CDCl$_3$:CD$_3$OD; 3:1, 500 MHz): δ 3.38 (dd, J=1.2, 12.1 Hz, 1H), 3.64 (dd, J=2.8, 12.1 Hz, 1H), 4.07 (dd, J=1.2, 2.8 Hz, 1H), 4.45 (d, J=8.2 Hz, 1H), 5.03 (d, J=12.7 Hz, 1H), 5.05 (d, J=12.7 Hz, 1H), 5.60 (d, J=8.2 Hz, 1H), 5.91 (d, J=8.2 Hz, 1H), 7.08-7.10 (m, 1H), 7.17-7.19 (m, 2H), 7.62 (dd, J=1.9, 6.8 Hz, 1H), 8.07 (d, J=8.2 Hz, 1H); $^{13}$C NMR (CDCl$_3$:CD$_3$OD; 3:1, 125 MHz): δ 60.4 (t), 72.2 (t), 78.1 (d), 86.0 (d), 87.7 (d), 94.8 (s), 102.2 (d), 120.6 (d), 123.1 (d), 127.6 (d), 128.6 (d), 134.9 (s), 140.9 (s), 142.0 (d), 151.3 (s), 164.3 (s) ppm; ESI-MS (m/z): 333.4 (18%, [M+H]$^+$), 355.3 (100%, [M+Na]$^+$), 371.3 (32%, [M+K]$^+$); Anal. Calcd for C$_{16}$H$_{16}$N$_2$O$_6$: C, 57.83; H, 5.85; N, 8.43%. Found: C, 57.51; H, 5.99; N, 8.21%.

Example 2

1-[3-C,3-O-(o-phenylenemethylene)-β-D-ribopyranosyl] uracil (21): By following procedure B, cycloaddition of the diyne 4 (100 mg, 0.55 mmol) with acetylene gave 21 (77 mg, 71% yield) as a White solid, mp: 138-140° C.; $[\alpha]_D^{25}$+56.5 (c 0.4, MeOH); IR (nujol) ν: 3393, 3018, 2961, 2854, 1679, 1459, 1377, 1243, 1062 cm$^{-1}$; $^1$H NMR (CD$_3$OD, 400 MHz): δ 3.85 (t, J=10.8 Hz, 1H), 3.94 (dd, J=5.4, 10.8 Hz, 1H), 4.03 (dd, J=5.4, 10.8 Hz, 1H), 4.06 (d, J=9.5 Hz, 1H), 5.22 (d, J=11.8 Hz, 1H), 5.27 (d, J=11.8 Hz, 1H), 5.73 (d, J=8.1 Hz, 1H), 5.86 (d, J=9.5 Hz, 1H), 7.25 (dd, J=6.1, 1.55 Hz, 1H), 7.30-7.35 (m, 2H), 7.38-7.40 (m, 1H), 7.79 (d, J=8.1 Hz, 1H); $^{13}$C NMR (CD$_3$OD, 100 MHz): d 68.8 (t), 71.4 (d), 72.7 (d), 75.8 (t), 83.7 (d), 93.9 (s), 103.2 (d), 121.8 (d), 122.3 (d), 128.6 (d), 129.4 (d), 139.5 (s), 142.9 (d), 143.0 (s), 152.9 (s), 166.1 (s) ppm; ESI-MS (m/z): 333.60 (19.12%, [M+1]$^+$), 355.60 (100%, [M+Na]$^+$), 371.57 (11.03%, [M+K]$^+$); Anal. Calcd for C$_{16}$H$_{16}$N$_2$O$_6$: C, 57.83; H, 4.85; N, 8.43%. Found: C, 57.95; H, 4.98; N, 8.56%.

Example 3

1-[3-C,3-O-{o-(3,4-acetyloxymethyl)phenylenemethylene}-β-D-ribofuranosyl]uracil (24): General procedure A was followed. Diyne 1 (100 mg, 0.33 mmol) and 1,4-Diacetoxy-2-butyne (0.24 mL, 1.63 mmol) were used to afford 24 (129 mg, 83% yield) as a White solid, mp: 181-183° C.; $[\alpha]_D^{25}$+25.0 (c 0.5, MeOH); IR (CHCl$_3$) ν: 3683, 3304, 3019, 2400, 1749, 1600, 1422, 1478, 1424, 1372, 1216, 1030, 928 cm$^{-1}$; $^1$H-NMR (CDCl$_3$:CD$_3$OD; 3:1, 500 MHz): δ 2.02 (s, 3H), 2.04 (s, 3H), 3.45 (dd, J=1.0, 11.8 Hz, 1H), 3.77 (dd, J=2.9, 12.0 Hz, 1H), 4.16 (dd, J=1.1, 2.7 Hz, 1H), 4.57 (d, J=8.2 Hz, 1H), 5.11 (d, J=12.7 Hz, 1H), 5.13 (d, J=2.4, 12.7 Hz, 1H), 5.15-5.17 (m, 4H), 5.16 (d, J=12.4 Hz, 1H), 5.71 (d, J=8.1 Hz, 1H), 5.95 (d, J=8.2 Hz, 1H), 7.78 (s, 1H), 8.09 (d, J=8.2 Hz, 1H); $^{13}$C NMR (CDCl$_3$:CD$_3$OD; 3:1, 125 MHz): δ 20.8 (q, 2C) 60.6 (t), 63.4 (t), 64.1 (t), 72.3 (t), 78.2 (d), 86.0 (d), 88.3 (d), 95.1 (s), 102.7 (d), 122.1 (d), 125.5 (d), 134.1 (s), 135.7 (s), 135.8 (s), 142.0 (s), 142.1 (s), 151.3 (s), 164.0 (s), 170.9 (s), 171.1 (s) ppm; ESI-MS (m/z): 477.4 (5.3%, [M+H]$^+$), 499.3 (100%, [M+Na]$^+$), 515.5 (3.5%, [M+K]$^+$); Anal. Calcd for C$_{22}$H$_{24}$N$_2$O$_{10}$: C, 55.46; H, 5.08; N, 5.88%. Found: C, 55.30; H, 5.21; N, 5.93%.

Example 4

1-[3-C,3-O-{o-(3,4-acetyloxymethyl)phenylenemethylene}-β-D-ribopyranosyl]uracil (27): Cycloaddition of diyne 4 (130 mg, 0.42 mmol) and 1,4-Diacetoxy-2-butyne (0.32 mL, 2.12 mmol) following procedure B gave 27 (164 mg, 81% yield) as a Liquid, $[\alpha]_D^{25}$+15.9 (c 0.4, MeOH); IR (CHCl$_3$) ν: 3687, 3650, 3567, 3019, 2930, 2400, 1732, 1693, 1612, 1517, 1474, 1423, 1386, 1216, 1075, 1028, 961, 928 cm$^{-1}$; $^1$H NMR (CDCl$_3$:CD$_3$OD; 3:1, 400 MHz): δ 1.87 (s, 6H), 3.62 (t, J=12.5 Hz, 2H), 3.67 (d, J=9.4 Hz, 1H), 3.75 (dd, J=1.8, 5.3 Hz, 1H), 3.78 (dd, J=1.8, 5.3 Hz, 1H), 4.99 (s, 2H), 5.00 (s, 2H), 5.52 (d, J=8.1 Hz, 1H), 5.59 (d, J=9.4 Hz, 1H), 7.08 (s, 1H), 7.12 (s, 1H), 7.33 (d, J=8.1 Hz, 1H); $^{13}$C NMR (CDCl$_3$:CD$_3$OD; 3:1, 100 MHz): δ 20.2 (q), 20.3 (q), 63.3 (t) 63.7 (t), 67.2 (t), 69.7 (t), 71.5 (d), 74.2 (t), 82.0 (d), 92.1 (s), 102.1 (d), 121.9 (d), 122.1 (d), 133.7 (s), 134.9 (s), 138.1 (s), 140.4 (d), 141.8 (s), 151.0 (s), 163.9 (s), 170.9 (s), 171.1 (s) ppm; ESI-MS (m/z): 477.9 (0.8%, [M+H]$^+$), 499.9 (100%, [M+Na]$^+$), 515.9 (1.3%, [M+K]$^-$); Anal. Calcd for C$_{22}$H$_{24}$N$_2$O$_{10}$: C, 55.46; H, 5.88; N, 5.88%. Found: C, 55.39; H, 5.96; N, 5.78%.

Example 5

1-[3-C,3-O-{o-(3/4-$^n$pentyl)phenylenemethylene}-β-D-ribofuranosyl]uracil (30): General procedure A was followed. Diyne 1 (120 mg, 0.39 mmol) and 1-heptyne (0.26 mL, 1.96 mmol) were used to afford 30 (126 mg, 80% yield) as a White solid, mp: 241-143° C.; IR (CHCl$_3$) ν: 3683, 3019, 2400, 1695, 1522, 1476, 1424, 1416, 1021, 908 cm$^{-1}$; $^1$H NMR (CDCl$_3$:CD$_3$OD; 3:1, 400 MHz): δ 0.85 (t, J=6.5 Hz, 3H), 1.27-1.29 (m, 6H), 1.56 (br.s, 3H), 2.57 (dd, J=7.6, 15.4 Hz, 2H), 3.54 (d, J=12.1 Hz, 1H), 3.76 (dd, J=3.0, 12.1 Hz, 1H), 4.18 (m, 1H), 4.57 (t, J=8.5 Hz, 1H), 5.12 (d, J=12.6 Hz, 1H), 5.16 (d, J=12.6 Hz, 1H), 5.72 (d, J=8.1 Hz, 1H), 6.01 (d, J=8.1 Hz, 1H), 7.03-7.15 (m, 2H), 7.56-7.64 (m, 1H), 8.18 (dd, J=1.3, 8.2 Hz, 1H); $^{13}$C NMR (CDCl$_3$:CD$_3$OD; 3:1, 100 MHz): δ 13.6 (q), 22.2 (t), 31.0 (t), 31.2 (t), 35.5 (t), 35.6 (t), 60.5 (t), 72.1 (t), 72.2 (t), 77.3 (s), 77.9 (s), 78.0 (d), 86.0 (2d), 88.0 (d), 88.1 (d), 94.7 (s), 102.2 (d), 120.3 (s), 120.4 (d), 122.9 (d), 128.0 (d), 128.9 (d), 132.1 (s), 135.0 (s), 138.2 (s), 141.1 (s), 142.1 (2d), 142.7 (d), 143.8 (s), 151.3 (s), 164.3 (s) ppm; ESI-MS (m/z): 403.2 (2.4%, [M+H]$^+$), 425.3 (100%, [M+Na]$^+$), 441.2 (4.5%, [M+K]$^+$); Anal. Calcd for C$_{21}$H$_{26}$N$_2$O$_6$: C, 62.67; H, 6.51; N, 6.96%. Found: C, 62.58; H, 6.60; N, 7.03%.

Example 6

1-[3-C,3-O-{o-(3/4-$^n$Pentyl)phenylenemethylene}-β-D-ribofuranosyl]thymine (31): By following procedure A, cycloaddition of the diyne 2 (100 mg, 0.31 mmol) with 1-heptyne (0.20 mL, 1.56 mmol) gave 31 (105 mg, 81% yield) as a White solid, mp: 210-212° C.; IR (CHCl$_3$) ν: 3685, 3308, 3020, 2400, 1521, 1476, 1423, 1385, 1215, 1100, 1068, 1044, 909, 770, 669, 651, 626 cm$^{-1}$; $^1$H NMR (CDCl$_3$:CD$_3$OD, 3:1, 400 MHz): δ 0.85 (t, J=6.1 Hz, 3H), 1.21-1.29 (m, 4H), 1.57 (br.s, 3H), 1.88 (s, 3H), 2.59 (dd, J=7.6, 15.4 Hz, 2H), 3.52 (d, J=12.1 Hz, 1H), 3.75 (d. J=12.1 Hz, 1H), 3.92 (br.s, 1H), 4.61 (t, J=6.8 Hz, 1H), 5.13 (2d, J=12.6 Hz, 2H), 5.94 (d, J=7.8 Hz, 1H), 7.02-7.12 (m, 2H), 7.46-7.65 (m, 2H), 7.90 (s, 1H); $^{13}$C NMR (CDCl$_3$:CD$_3$OD, 3:1, 100 MHz): δ 11.9 (q), 13.6 (q), 22.2 (t), 31.0 (t), 31.2 (t, 2C), 35.5 (t), 35.6 (t), 60.5 (t), 72.1 (t), 72.2 (s), 77.2 (s), 77.9 (s), 78.0 (d), 86.0 (2d), 88.0 (d), 88.1 (d), 94.7 (s), 102.2 (d), 120.3 (s), 120.4 (d), 122.9 (d), 128.0 (d), 128.9 (d), 132.1 (s), 135.0 (s), 138.2 (s), 141.1 (s), 142.1 (2d), 142.7 (s), 143.8 (s), 151.3 (s), 164.3 (s) ppm; ESI-MS (m/z): 417.4 (39%, [M+H]$^+$), 439.4 (100%, [M+Na]$^+$), 455.2 (9%, [M+K]$^+$); Anal. Calcd for $C_{22}H_{28}N_2O_6$: C, 63.45; H, 6.78; N, 6.73%. Found: C, 63.37; H, 6.83; N, 6.82%.

Example 7

1-[3-C,3-O-{o-(3/4-″pentyl)phenylenemethylene}-β-D-ribopyranosyl]uracil (33): General procedure A was followed. Diyne 4 (120 mg, 0.39 mmol) 1-heptyne (0.28 mL, 1.95 mmol) were used to afford a 33 (112 mg, 81% yield) as a Liquid, $[α]_D^{25}$+31.0 (c 1.7, MeOH); IR (CHCl$_3$) v: 3672, 3565, 3020, 2929, 2400, 1696, 1634, 1539, 1403, 1215, 105, 1029, 929 cm$^{-1}$; $^1$H NMR (CDCl$_3$:CD$_3$OD; 3:1, 400 MHz): δ 0.82 (t, J=6.4 Hz, 3H), 1.22-1.32 (m, 6H), 2.51-2.61 (m, 2H), 3.73-3.70 (m, 2H), 3.85-4.98 (m, 2H), 5.17 (d, J=12.1 Hz, 1H), 5.27 (d, J=12.1 Hz, 1H), 5.65 (dt, J=1.9, 8.2 Hz, 1H), 5.79 (d, J=8.2 Hz, 1H), 7.00 (d, J=4.0 Hz, 1H), 7.09-7.11 (m, 2H), 7.33 (dd, J=1.9, 8.2 Hz, 1H), 9.68 (br.s, 1H); $^{13}$C NMR (CDCl$_3$:CD$_3$OD; 3:1, 100 MHz): δ 13.9 (q), 14.0 (q), 22.3 (t), 22.5 (t), 22.6 (t), 29.2 (t), 31.1 (2t), 31.2 (t), 31.5 (t), 31.7 (t), 35.8 (t), 35.7 (t), 51.0 (t), 67.8 (t), 70.1 (d), 70.2 (d), 72.6 (d), 72.7 (d), 74.9 (t), 77.2 (d), 82.2 (d), 92.0 (s), 102.8 (d), 120.3 (d), 120.4 (d), 120.5 (d), 120.7 (d), 128.1 (d), 128.9 (d), 134.4 (s), 137.3 (s), 138.1 (s), 139.6 (d), 141.0 (s), 142.7 (s), 143.6 (s), 151.0 (s), 163.0 (s) ppm; ESI-MS (m/z): 403.3 (9%, [M+H]$^+$), 425.4 (100%, [M+Na]$^+$), 471.5 (18%, [M+K]$^+$); Anal. Calcd for $C_{21}H_{26}N_2O_6$: C, 62.67; H, 6.51; N, 6.96%. Found: C, 62.76; H, 6.49; N, 6.82%.

Example 8

1-[3-C,3-O-{o-(2,4-Diphenyl)phenylenemethylene}-β-D-ribofuranosyl]uracil (54): By following procedure C, cycloaddition of the diyne 36 (20 mg, 0.052 mmol) with phenyl acetylene (0.005 mL, 0.052 mmol) gave 54 (22 mg, 85%) as a White solid, mp: 270-272° C.; $[α]_D^{25}$+35.0 (c 0.3, CHCl$_3$); IR (CHCl$_3$) v: 3020, 2925, 1694, 1526, 1046, 929, 669 cm$^{-1}$; $^1$H NMR (CDCl$_3$+CD$_3$OD, 400 MHz): δ 3.29 (dd, J=6.6, 12.1 Hz, 1H), 3.35 (dd, J=4.0, 12.1 Hz, 1H), 4.20 (dd, J=4.2, 6.4 Hz, 1H), 4.47 (d, J=8.2 Hz, 1H), 5.25 (s, 2H), 5.58 (d, J=8.2 Hz, 1H), 6.07 (d, J=8.1 Hz, 1H), 6.85 (d, J=8.2 Hz, 1H), 7.36-7.51 (m, 10H), 7.60 (dd, J=1.2, 7.3 Hz, 2H): $^{13}$C NMR (CDCl$_3$+CD$_3$OD, 100 MHz): δ 61.8 (t), 70.4 (t), 76.4 (d), 85.4 (d), 86.6 (d), 93.1 (s), 102.7 (d), 118.8 (d), 127.0 (3C, d), 127.8 (d), 128.0 (d), 128.3 (d), 128.7 (2C, d), 129.4 (2C, d), 130.0 (s), 130.8 (d), 138.5 (s), 139.5 (s), 139.8 (s), 139.8 (d), 142.0 (s), 142.9 (s), 151.0 (s), 163.7 (s) ppm; ESI-MS (m/z): 507.02 (70%, [M+Na]$^+$), 522.97 (100%, [M+K]$^+$); Anal. Calcd for $C_{28}H_{24}N_2O_6$: C, 69.41; H, 4.99; N, 5.78%. Found: C, 69.30; H, 5.18; N, 5.87%.

Example 9

1-[3-C,3-O-{o-(2-Phenyl-4-″henicosyl)phenylenemethylene}-β-D-ribofuranosyl]uracil (56): General procedure C was followed. Diyne 36 (20 mg, 0.052 mmol) and 1-tricosyne (15.9 mg, 0.052 mmol) were used to afford 56 (32 mg, 87% yield) as a Colorless gum, $[α]_D^{25}$+26.9 (c 0.3, CHCl$_3$); IR (CHCl$_3$) v: 2924, 2853, 1686, 1466, 1385, 1046, 929, 669 cm$^{-1}$; $^1$H NMR (CDCl$_3$, 200 MHz): δ 0.86 (t, J=6.4 Hz, 3H), 1.24 (m, 36H), 1.52-1.70 (m, 2H), 2.62 (t, J=7.7 Hz, 2H), 3.28 (d, J=2.8 Hz, 2H), (m, 3H), 4.10 (t, J=4.5 Hz, 1H), 4.50 (dd, J=8.1, 10.5 Hz, 1H), 5.13 (s, 2H), 5.57 (d, J=1.9, 8.1 Hz, 1H), 6.08 (d, J=8.0 Hz, 1H), 6.96 (d, J=1.2 Hz, 1H), 7.04 (d, 8.0 Hz, 1H), 7.09 (d, J=1.2 Hz, 1H), 7.41-7.49 (m, 5H); $^{13}$C NMR (CDCl$_3$, 100 MHz): δ 14.1 (q), 22.7 (t), 29.3 (2C, t), 29.4 (t), 29.6 (t), 29.7 (12C, t), 31.3 (t), 31.9 (t), 35.5 (t), 61.8 (t), 70.3 (t), 77.2 (s), 76.8 (d), 84.6 (d), 87.2 (d), 93.7 (s), 103.0 (d), 120.5 (d), 128.3 (d), 128.7 (2C, d), 129.3 (2C, d), 131.4 (d), 138.1 (s), 140.0 (s), 140.1 (d), 142.5 (s), 144.5 (s), 150.8 (s), 162.9 (s); ESI-MS (m/z): 725.3 (80%, [M+Na]), 741.20 (100%, [M+K]$^+$); Anal. Calcd for $C_{43}H_{62}N_2O_6$: C, 73.47; H, 8.89; N, 3.99%; Found: C, 73.38; H, 8.97; N, 4.10%.

Example 10

1-[3-C,3-O-{o-(2-phenyl-4-chloropropyl)phenylenemethylene}-β-D-ribofuranosyl]uracil (57): Procedure C was followed. Diyne 36 (20 mg, 0.052 mmol) and 1-chloro-4-pentyne (5.33 mmL, 0.052 mmol) were used to afford 57 (21.0 mg, 83% yield) as a White solid, mp: 172-174° C.; $[α]_D^{25}$+12.7 (c 0.7, CHCl$_3$); IR (CHCl$_3$) v: 669.1, 928.7, 1046.4, 1215.7, 1385.22, 1462.17, 1694.16, 2924.8, 3020.1 cm$^{-1}$; $^1$H NMR (CDCl$_3$, 400 MHz): δ 2.08 (quin, J=6.8 Hz, 2H), 2.82 (t, J=7.5 Hz, 2H), 3.23 (dd, J=5.8, 12.1 Hz, 1H), 3.30 (dd, J=3.3, 12.1 Hz, 1H), 3.53 (t, J=6.3 Hz, 2H), 3.70 (d, J=8.9 Hz, 1H), 4.11 (t, J=4.5 Hz, 1H), 4.47 (br t, J=7.4 Hz, 1H), 5.12 (s, 2H), 5.55 (d, J=8.0 Hz, 1H), 6.06 (d, J=8.0 Hz, 1H), 6.95 (d, J=8.2 Hz, 1H), 6.96 (s, 1H), 7.10 (s, 1H), 7.36-7.48 (m, 5H), 9.45 (br s, 1H); $^{13}$C NMR (CDCl$_3$, 100 MHz): δ 32.22 (t), 33.68 (t), 44.06 (t), 61.89 (t), 70.32 (t), 77.20 (s), 84.88 (d), 87.03 (d), 93.53 (s), 102.99 (d), 120.63 (d), 128.27 (d), 128.64 (2C, d), 129.36 (2C, d), 129.54 (d), 131.42 (d), 138.37 (s), 139.76 (s), 140.02 (d), 142.07 (s), 142.73 (s), 150.96 (s), 163.22 (s); ESI-MS (m/z): 507.54 (100%, [M+Na]$^+$); Anal. Calcd for $C_{25}H_{25}ClN_2O_6$: C, 61.92; H, 5.20; Cl, 7.31; N, 5.78%. Found: C, 61.82; H, 5.07; N, 5.88%.

Example 11

1-[3-C,3-O-{o-(2-phenyl-4-phthalimidomethyl)phenylenemethylene}-β-D-ribofuranosyl]uracil (58): General procedure C was followed. Diyne 36 (20 mg, 0.052 mmol) and N-propargyl pthalimide (9.4 mg, 0.052 mmol) were used to afford 58 (23.7 mg, 80% yield) as a White solid, mp: 196-198° C.; $[α]_D^{25}$+8.2 (c 1.6, CHCl$_3$); IR (CHCl$_3$) v: 669.1, 928.7, 946.8, 1046.6, 1107.3, 1215.8, 1345.5, 1394.2, 1468.5, 1716.8, 1770.6, 2928.6, 3019.9, 3393.1 cm$^{-1}$; $^1$H NMR (CDCl$_3$, 200 MHz): δ 3.15-3.33 (m, 2H), 3.48 (br s, 1H), 4.07 (t, J=4.9 Hz, 1H), 4.44 (br s, 1H), 4.82 (d, J=15.0 Hz, 1H), 4.89 (d, J=15.0 Hz, 1H), 5.09 (s, 2H), 5.52 (d, J=8.1 Hz, 1H), 6.02 (d, J=8.0 Hz, 1H), 6.94 (d, J=8.1 Hz, 1H), 7.20 (d, J=1.3 Hz, 1H), 7.33 (d, J=1.3 Hz, 1H), 7.36-7.49 (m, 5H), 7.66-7.75 (m, 2H), 7.79-7.88 (m, 2H), 9.15 (br s, 1H); $^{13}$C NMR (CDCl$_3$, 50 MHz): δ 40.87 (t), 61.74 (t), 70.22 (t), 76.64 (s), 84.72 (d), 87.01 (d), 93.61 (s), 102.96 (d), 120.74 (d), 123.51 (3C, d), 128.40 (d), 128.67 (2C, d), 129.38 (2C, d), 131.33 (d), 131.89 (s), 134.18 (3C, d), 137.51 (s), 138.70 (s), 139.35 (s), 139.95 (s), 143.07 (s), 150.85 (s), 163.00 (s), 167.96 (2C, s); ESI-MS (m/z): 590.41 (100%, [M+Na]$^+$); Anal. Calcd for $C_{31}H_{25}N_3O_8$: C, 65.60; H, 4.44; N, 7.40%. Found: C, 65.51; H, 4.31; N, 7.31%.

Example 12

1-[3-C,3-O-{o-(2-phenyl-4-(3-aminophenyl))phenylenemethylene}-β-D-ribofuranosyl]uracil (59): By following procedure C, cycloaddition of the diyne 36 (20 mg, 0.052 mmol) with 3-amino phenyl acetylene (3.77 mmL, 0.052 mmol) gave 59 (22.2 mg, 85% yield) as a Yellowish liquid, $[\alpha]_D^{25}$+15.8 (c 0.5, CHCl$_3$); IR (CHCl$_3$) v: 669.2, 928.9, 1018.4, 1215.7, 1385.1, 1523.9, 1694.6, 2924.8, 3020.1, 3437.0 cm$^{-1}$; $^1$H NMR (CDCl$_3$+CD$_3$OD, 400 MHz): δ 3.07 (dd, J=7.3, 11.9 Hz, 1H), 3.14 (dd, 4.2, 11.9 Hz 1H), 4.04 (dd, J=4.2, 7.3 Hz, 1H), 4.28 (d, J=8.2 Hz, 1H), 5.04 (d, J=13.0 Hz, 1H), 5.08 (d, J=13.0 Hz, 1H), 5.09 (s, 2H), 5.40 (d, J=8.1 Hz, 1H), 5.90 (d, J=8.2 Hz, 1H), 6.58 (dd, J=1.8, 8.2 Hz, 1H), 6.60 (d, J=1.3, 8.1 Hz, 1H), 6.80 (s, 1H), 6.84 (d, J=7.8 Hz, 1H), 7.05 (t, J=7.8 Hz, 1H), 7.16 (s, 1H), 7.30 (s, 6H); $^{13}$C NMR (CDCl$_3$+CD$_3$OD, 100 MHz): δ 61.73 (t), 70.21 (t), 76.15 (d), 85.45 (d), 86.33 (d), 92.68 (s), 102.37 (d), 113.86 (d), 114.86 (d), 117.49 (d), 118.50 (d), 127.69 (d), 127.98 (2C, d), 129.33 (2C, d), 129.40 (d), 129.64 (d), 130.66 (s), 138.13 (s), 139.68 (d), 139.72 (s), 140.45 (s), 141.87 (s), 142.55 (s), 146.29 (s), 150.88 (s), 163.83 (s); ESI-MS (m/z): 622.44 (100%, [M+Na]$^+$); Anal. Calcd for: C$_{28}$H$_{25}$N$_3$O$_6$: C, 67.33; H, 5.04; N, 8.41%. Found: C, 67.31; H, 4.97; N, 8.53%.

Example 13

1-[3-C,3-O-{o-(2-″hexyl-4-phenyl)phenylenemethylene}-β-D-ribofuranosyl]uracil (60): Procedure C was followed. Diyne 37 (50 mg, 0.128 mmol) and phenyl acetylene (13.07 mmL, 0.128 mmol) were used to afford 60 (49.2 mg, 78% yield) as a white solid, mp: 143-145° C.; $[\alpha]_D^{25}$+20.9 (c 0.5, CHCl$_3$); IR (CHCl$_3$) v: 669.3, 929.0, 1045.5, 1384.9, 1466.2, 1685.8, 2852.7, 2923.9 cm$^{-1}$; $^1$H NMR (CDCl$_3$, 200 MHz): δ 0.88 (t, J=6.5 Hz, 3H), 1.26-1.47 (m, 6H), 1.56-1.76 (m, 2H), 2.65-2.89 (m, 2H), 3.51 (dd, J=3.9 Hz, 2H), 3.81 (dd, J=7.5, 12.1 Hz, 1H), 4.38 (dd, J=3.9, 7.2 Hz, 1H), 4.62 (d, J=8.1 Hz, 1H), 5.14 (d, J=12.7 Hz, 1H), 5.22 (d, J=12.7 Hz, 1H), 5.80 (dd, J=1.5, 8.1 Hz, 1H), 5.91 (d, J=8.0 Hz, 1H), 7.37-7.57 (m, 7H), 9.33 (br s, 1H) ppm; $^{13}$C NMR (CDCl$_3$, 50 MHz): δ 14.06 (q), 22.62 (t), 29.73 (t), 31.68 (t), 31.94 (t), 33.52 (t), 61.70 (t), 71.97 (t), 76.38 (d), 86.52 (d), 89.16 (d), 92.26 (s), 103.20 (d), 117.50 (d), 127.15 (2C, d), 127.71 (d), 128.57 (d), 128.84 (2C, d), 132.26 (s), 138.02 (s), 140.28 (s), 140.38 (d), 141.59 (s), 142.56 (s), 150.76 (s), 163.00 (s); ESI-MS (m/z): 515.65 (100%, [M+Na]$^+$); Anal. Calcd for C$_{28}$H$_{32}$N$_2$O$_6$: C, 68.28; H, 6.55; N, 5.69%. Found: C, 68.17; H, 6.47, N, 5.73%.

Example 14

1-[3-C,3-O-{o-(2-″hexyl-4-″hexyl)phenylenemethylene}-β-D-ribofuranosyl]uracil (61): General procedure C was followed. Diyne 37 (20 mg, 0.051 mmol) and 1-octyne (7.55 mmL, 0.051 mmol) were used to afford a 61 (19.2 mg, 75% yield) as a Colorless liquid, $[\alpha]_D^{25}$+4.4 (c 0.5, CHCl$_3$); IR (CHCl$_3$) v: 669.1, 928.9, 1045.1, 1215.6, 1385.0, 1461.8, 1521.2, 1697.5, 2858.4, 2929.9, 3020.1 cm$^{-1}$; $^1$H NMR (CDCl$_3$, 400 MHz): δ 0.87 (t, J=6.4 Hz, 3H), 0.88 (t, J=6.4 Hz, 3H), 1.26-1.38 (m, 12H), 1.53-1.71 (m, 4H), 2.47 (dd, J=7.7, 8.1 Hz, 2H), 2.60-2.66 (m, 1H), 2.72-2.74 (m, 1H), 3.43 (dd, J=3.8, 12.0 Hz, 1H), 3.75 (dd, J=7.6, 12.0 Hz, 1H), 4.32 (dd, J=3.8, 7.6 Hz, 1H), 4.56 (t, J=7.8 Hz, 1H), 5.05 (d, J=12.4 Hz, 1H), 5.12 (d, J=12.4 Hz, 1H), 5.76 (d, J=8.0 Hz, 1H), 5.87 (d, J=8.0 Hz, 1H), 6.85 (s, 1H), 6.95 (s, 1H), 7.45 (d, 8.0 Hz, 1H), 9.25 (br s, 1H); $^{13}$C NMR (CDCl$_3$, 100 MHz): δ 14.05 (q), 14.15 (q), 22.55 (t), 22.62 (t), 28.97 (t), 29.69 (t), 31.35 (t), 31.64 (t), 31.68 (t), 31.89 (t), 33.40 (t), 35.61 (t), 61.76 (t), 71.95 (t), 76.28 (d), 86.53 (d), 89.13 (d), 92.09 (s), 103.15 (d), 118.70 (d), 129.66 (d), 130.42 (s), 137.24 (s), 140.33 (d), 140.84 (s), 144.39 (s), 150.69 (s), 162.92 (s) ESI-MS (m/z): 523.27 (100%, [M+Na]$^+$); Anal.

Calcd for: C$_{28}$H$_{40}$N$_2$O$_6$: C, 67.18; H, 8.05; N, 5.60%; Found: C, 67.06; H, 7.97; N, 5.71%.

Example 15

1-[3-C,3-O-{o-(2-″Hexyl-4-″henicosyl)-phenylenemethylene}-β-D-ribofuranosyl]uracil (62): General procedure C was followed. Diyne 37 (50 mg, 0.138 mmol) and 1-tricosyne (42.3 mg, 0.138 mmol) were used to afford compound 62 (66.5 mg, 73% yield) as a colorless liquid. $[\alpha]_D^{25}$+1.9 (c 0.2, CHCl$_3$); IR (CHCl$_3$) v: 3020, 2930, 2858, 1698, 1521, 1462, 1385, 1216, 1045, 929, 669 cm$^{-1}$; $^{1H}$ NMR (CDCl$_3$, 200 MHz): δ 0.86 (t, J=6.5 Hz, 3H), 0.88 (t, J=6.5 Hz, 3H), 1.24 (s, 36H), 1.30-1.36 (m, 8H), 2.57 (t, J=7.7 Hz, 2H), 2.60-2.66 (m, 1H), 2.70-2.79 (m, 1H), 3.33 (br s, 1H), 3.44 (dd, J=4.0, 12.1 Hz, 1H), 3.75 (dd, J=7.7, 12.1 Hz, 1H), 4.32 (dd, J=4.0, 7.1 Hz, 1H), 4.59 (t, J=7.8 Hz, 1H), 5.07 (d, J=12.1 Hz, 1H), 5.13 (d, J=12.1 Hz, 1H), 5.29 (s, 1H), 5.78 (d, J=8.1 Hz, 1H), 5.85 (d, J=8.1 Hz, 1H), 6.86 (s, 1H), 6.96 (s, 1H), 7.44 (d, J=8.0 Hz, 1H), 8.94 (br s, 1H); $^{13}$C NMR (CDCl$_3$, 50 MHz): δ 14.0 (q), 14.1 (q), 22.6 (t), 22.7 (t), 29.3 (t), 29.5 (t), 29.6 (t), 29.7 (13C, t), 31.4 (t), 31.7 (t), 31.9 (t), 31.9 (t), 33.4 (t), 35.6 (t), 53.4 (t), 61.8 (t), 72.0 (t), 76.2 (d), 86.4 (d), 89.3 (d), 92.1 (s), 103.2 (d), 118.7 (d), 129.7 (d), 130.3 (s), 137.3 (s), 140.4 (d), 140.8 (s), 144.5 (s), 150.6 (s), 162.7 (s) ppm; ESI-MS (m/z): 733.51 (10%, [M+Na]$^+$); Anal. Calcd for C$_{43}$H$_{70}$N$_2$O$_6$: C, 72.64; H, 9.92; N, 3.94. Found: C, 72.51; H, 9.97; N, 4.01%.

Example 16

1-[3-C,3-O-{o-(2-phenyl-4-″hexyl)phenylenemethylene}-β-D-ribopyranosyl]uracil (65): General procedure C was followed. Cycloaddition of the diyne 38 (25 mg, 0.065 mmol) with 1-octyne (7.2 mmL, 0.065 mmol) gave compound 65 (24.8 mg, 77% yield) as a white solid. mp: 124-126° C.; $[\alpha]_D^{25}$+85.4 (c 1.1, CHCl$_3$); IR (CHCl$_3$) v: 2924, 2853, 1686, 1466, 1385, 1046, 929, 669 cm$^{-1}$; $^1$H NMR (CDCl$_3$, 400 MHz): δ 0.87 (t, J=6.6 Hz, 3H), 1.27-1.40 (m, 6H), 1.60 (quint, J=7.8, 2H), 2.60 (t, J=7.8 Hz, 2H), 3.48 (br s, 1H), 3.58 (br s, 1H), 3.65 (t, J=10.5 Hz, 1H), 3.71 (dd, J=5.6, 10.5 Hz, 1H), 5.23 (d, J=12.3 Hz, 1H), 5.45 (d, J=12.3 Hz, 1H), 5.61 (d, J=8.2 Hz, 1H), 5.74 (d, J=9.3 Hz, 1H), 6.74 (d, J=8.4 Hz, 1H), 6.94 (s, 1H), 7.03 (s, 1H), 7.32-7.43 (m, 5H), 9.58 (s, 1H); $^{13}$C NMR (CDCl$_3$, 100 MHz): δ 14.1 (q), 22.5 (t), 22.7 (t), 31.3 (t), 31.6 (t), 35.6 (t), 67.0 (t), 69.4 (d), 73.0 (d), 74.3 (t), 81.8 (d), 93.3 (s), 103.2 (d), 119.9 (d), 128.0 (3C, d), 129.2 (2C, d), 130.1 (d), 130.1 (s), 137.5 (s), 139.0 (d), 139.3 (s), 141.3 (s), 143.7 (s), 151.1 (s), 163.0 (s); ESI-MS (m/z): 515.08 (75%, [M+Na]$^+$), 531.02 (100%, [M+K]$^+$); Anal. Calcd for C$_{28}$H$_{32}$N$_2$O$_6$: C, 68.28; H, 6.55; N, 5.69. Found: C, 68.31; H, 6.60; N, 5.76.

Example 17

1-[3-C,3-O-{o-(2-phenyl-4-chloropropyl)phenylenemethylene}-β-D-ribopyranosyl]uracil (67): General procedure C was followed. Diyne 38 (20 mg, 0.052 mmol) and 1-chloro-4-pentyne (5.51 mmL, 0.052 mmol) were used to afford compound 67 (20 mg, 79% yield) as a white solid. mp: 176-178° C.; $[\alpha]_D^{25}$+114.2 (c 0.5, CHCl$_3$); IR (CHCl$_3$) v: 3020, 2925, 1694, 1462, 1385, 1215, 1046, 929, 669 cm$^{-1}$; $^1$H NMR (CDCl$_3$CD$_3$OD, 500 MHz): δ 1.98 (quint, J=7.5 Hz, 2H), 2.70 (t, J=7.5 Hz, 2H), 3.24 (d, J=9.5 Hz, 1H), 3.45 (t, J=6.4 Hz, 2H), 3.51 (t, J=8.3 Hz, 1H), 3.61 (d, J=12.1 Hz, 1H), 3.65 (d, J=12.1 Hz, 1H), 5.14 (s, 2H), 6.55 (d, J=8.2 Hz, 1H), 5.60 (d, J=9.5 Hz, 1H), 6.67 (d, J=8.2 Hz, 1H), 6.85 (s, 1H), 6.98 (s, 1H), 7.24-7.33 (m, 5H); $^{13}$C NMR (CDCl$_3$+CD$_3$OD, 125 MHz): δ 32.2 (t), 33.7 (t), 44.0 (t), 66.9 (t), 69.4 (d), 71.4 (d), 73.8 (t), 81.6 (d), 92.8 (s), 102.7 (d), 119.9 (d), 127.7 (2C, d), 127.8 (d), 128.8 (2C, d), 129.7 (d), 131.3 (d), 137.4 (s), 139.1 (s), 139.3 (s), 141.0 (s), 141.9 (s), 151.1 (s), 163.7 (s); ESI-MS (m/z): 506.98 (60%, [M+Na]$^+$), 522.94 (100%, [M+K]$^+$); Anal. Calcd for C$_{25}$H$_{25}$ClN$_2$O$_6$: C, 61.92; H, 5.20; Cl, 7.31; N, 5.78% Found: C, 61.88; H, 5.09; Cl, 7.47; N, 5.81%.

ADVANTAGES OF PRESENT INVENTION

A strategy that integrates the conceptual advantages of DOS and the manipulation of chemical functionality at an advanced stage in a target oriented synthesis could be a valuable tool in new drug discovery programs. This needs the identification of a structurally simplifying transform(s) at the beginning of the retrosynthetic scheme. This transform(s) should comprise multiple bond disconnections resulting in a couple of retrons, amongst which at least one should be easy to access and manipulate. This provision of manipulation/substrate flexibility at the final/penultimate steps in the forward synthesis should address the chemical functionality modulation. We exemplify the potential of such an approach by selecting C(3)-spironucleosides as the targets, wherein the critical spiroannulation has been executed as the final step and employing commercial or easily available reagents as the substrates.

What is claimed is:
1. A process for the preparation of Spiro annulated nucleoside of general Formula I;

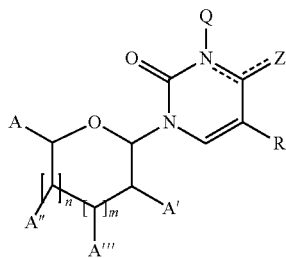

where, R (in the base) is selected from H, C$_1$-C$_4$ alkyl, halogen, OR, NHR (R═H, COCH$_3$, COO$^t$Bu); Q═H with the proviso that C—N double bond is absent, C—Z double bond is present and Z is O; Z is NH$_2$ with the proviso that C—Z double bond is absent, Q≠H; Z is O with the proviso that C—N double bond is absent;
A and A' are selected from H, lower alkyl-OH, —Oac, —CH$_2$OH, —CH$_2$OAc, —CH$_2$, OPiv, —CH$_2$OTBS; m and n are integers 0,1;
A" and A''' are selected from 1,3-dihydroisobenzofuran (1a) or isochroman [3,4-dihydro-1H-benzo[c] pyran] represented by the formula (1b), where R, R', R" are selected from H, —OH, halo group, —CH$_2$OH, —CH$_2$OAc, —COOH, —COOMe, C1-C30 straight or branched alkyl group, optionally substituted with halogen or —OH or —NH2 or —NPhth; phenyl group optionally substituted with halogen, amino, nitro, C1-C6 alkyl;
with the proviso that when n=1[i.e(CH$_2$)n=1] and where m=0[i.e(CH$_2$)m=0], A''' is absent and A" is 1,3-dihydro isobenzofuran (1a) or isochroman [3,4-dihydro-1H-benzo[c] pyran] represented by the formula (1b),

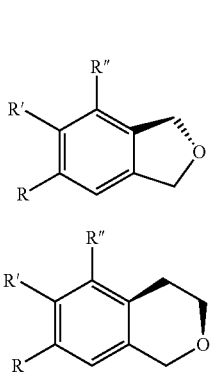

directly annulated at C-3, A and A' are selected from H, lower alkyl, OH, —OAc, —CH$_2$OH, —CH$_2$OAc, —CH$_2$OPiv, —CH$_2$OTBS; and R, R' and R" in 1,3-dihydro isobenzofuran (1a) or isochroman [3,4-dihydro-1H-benzo[c] pyran] represented by the formula (1b) are selected from H, —OH, halo group, —CH$_2$OH, —CH$_2$OAc, —COOH, —COOMe, C1-C30 straight or branched alkyl group, optionally substituted with halogen or —OH or NH$_2$ or —NPhth; phenyl group optionally substituted with halogen, amino, nitro, C1-C6 alkyl; R (in the base) is selected from H, C1-C4 alkyl, halogen; Q=H with the proviso that C—N double bond (....) is absent, C—Z double bond (....) is present and Z is O; Z is NH$_2$ with the proviso that C—Z double bond is absent, Q≠H; Z is O with the proviso that C—N double bond (....) is absent;
wherein the process comprises the steps of;
a) Preparing solution of diyne of formula

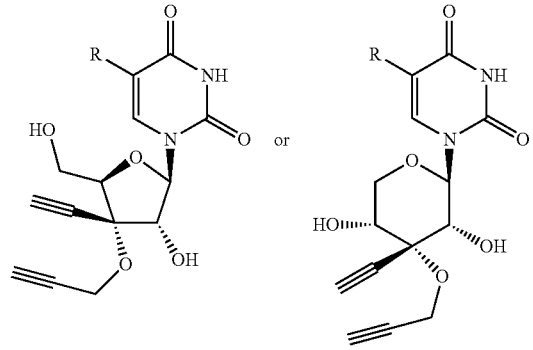

and alkyne in mole ratio ranging between 1:1 to 1:3 in a solvent followed by degassing of solution with dry argon, wherein said diyne used is selected from the group consisting of furanoside nucleoside, pyranoside nucleoside (1-[3-C-phenylethynyl-3-O-(2-propynyl)-β-D-ribo-pentofuranosyl]uracil), (1-[3-C-(1-octynyl)-3-O-(2-propynyl)-β-D-ribo-pentofuranosyl]uracil), (1[3-C-phenylethynyl-3-O-(2-propynyl)-β-D-ribopyranosyl]uracil), 1-[3-C-Propynyl/Phenylpropynyl/ "Hexylpropynyl-3-O-(2-propynyl)-β-D-ribo-pentofuranosyl]5-flurouracil), (1[3-C-Propynyl/ Phenylpropynyl/"Hexylpropynyl-3-O-(2-propynyl)-β-D-ribopyranosyl]5-fluoruracil);
b) adding a catalyst in mole ratio ranging between 0.02 to 0.05 into the degassed solution as obtained in step (a) followed by heating at temperature in the range of 70° C.-90° C. for a period in the range of 6 h-12 h;

c) cooling the solution as obtained in step (b) to room temperature ranging between 25° C.-30° C. followed by solvent evaporation and purification to obtain spiroannulated nucleoside.

2. A process for the preparation of Spiro annulated nucleoside of general Formula I as claimed in claim 1, wherein the process comprises the steps of;
a) charging of diyne of formula

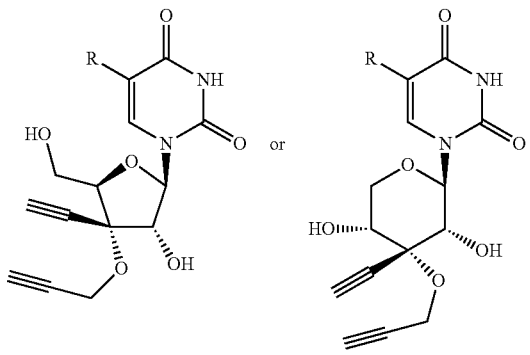

in a solvent in a sealed tube followed by degassing with alkyne, wherein said diyne used is step (a) is selected from the group consisting of furanoside nucleoside, pyranoside nucleoside (1-[3-C-phenylethynyl-3-O-(2-propynyl)-β-D-ribo-pentofuranosyl]uracil), (1-[3-C-(1-octynyl)-3-O-(2-propynyl)-β-D-ribo-pentofuranosyl]uracil), (1[3-C-phenylethynyl-3-O-(2-propynyl)-β-D-ribopyranosyl]uracil), 1-[3-C-Propynyl/Phenylpropynyl/"Hexylpropynyl-3-O-(2-propynyl)-β-D-ribo-pentofuranosyl]5-flurouracil), (1[3-C-Propynyl/Phenylpropynyl/"Hexylpropynyl-3-O-(2-propynyl)-β-D-ribopyranosyl]5-flurouracil);
b) adding a catalyst into the solution as obtained in step (a);
c) cooling the reaction mixture as obtained in step (b) at temperature ranging between −80° C.--70° C. followed by bubbling of alkyne for a period ranging between 25 min. to 60 min and sealing of tube;
d) transferring the sealed tube as obtained in step (c) in a steal bomb and heating at temperature ranging between 70° C.-90° C. for a period ranging between 6 h-12 h allowed by cooling to room temperature ranging between 25° C.-30° C.;
e) evaporating the solvent from reaction mixture as obtained in step (d) and purification to obtain spiroannulated nucleoside.

3. The process as claimed in claim 2, wherein the said alkyne used in step (a) and also in step (c) of claim 2 is symmetrical or unsymmetrical alkyne selected from the group consisting of acetylene(CH≡CH), terminal alkyne of the formula R—C≡CH where R is selected from C1-C30 straight or branched alkyl groups optionally substituted with halo, —OH, —OAc, —CH₂OH; a phenyl group further optionally substituted with lower alkyl, halo, —OH, —OAc; diacetate of 2-butyne-1,4-diol, an alkyne of the formula R"—C≡C—R'" where R" and R'" are selected from either straight or branched chain alkyl group, —H₂OH, —CH₂OAc, —COOH, —COOAc, TMS,N-propyne pthalimide.

4. The process as claimed in claim 1, wherein the said alkyne used in step (a) and also in step (c) of claim 2 is symmetrical or unsymmetrical alkyne selected from the group consisting of acetylene(CH≡CH), terminal alkyne of the formula R—C≡CH where R is selected from C1-C30 straight or branched alkyl groups optionally substituted with halo, —OH, —OAc, —CH₂OH; a phenyl group further optionally substituted with lower alkyl, halo, —OH, —OAc; diacetate of 2-butyne-1,4-diol, an alkyne of the formula R"—C≡C—R'" where R" and R'" are selected from either straight or branched chain alkyl group, —H₂OH, —CH₂OAc, —COOH, —COOAc, TMS,N-propyne pthalimide.

5. The process as claimed in claim 1, wherein 1,3-dihydroisobenzofuran is appended on the sugar moiety of the nucleoside via [2+2+2] cyclotrimerization reaction.

6. The process as claimed in claim 1, wherein isochroman [3,4-dihydro-1H-benzo[c] pyran] is appended on the sugar moiety of the nucleoside via [2+2+2] cyclotrimerization reaction.

7. The process as claimed in claim 1, wherein the spiroannulation of the nucleoside diyne with the symmetrical and unsymmetrical alkyne takes place at C-3 of the furanoside ring.

8. The process as claimed in claim 1, wherein the spiroannulation of the nucleoside diyne with the symmetrical and unsymmetrical alkyne takes place at C-3 of the pyranoside ring.

9. The process as claimed in claim 1, wherein catalyst used in step (b) is selected from Wilkinson's catalyst [RhCl(PPh₃)₃], Cp*RuCl(cod) and [Rh(cod)2]BF4/(R)-BINAP.

10. The process as claimed in claim 1, wherein solvent used in step (a) is selected from the group consisting of toluene, xylene, methanol, ethanol, propanols and mixture thereof.

11. The process as claimed in claim 1, wherein yield of spiroannulated nucleoside is in the range of 71-87%.

12. A process for the preparation of Spiro annulated nucleoside of general Formula I;

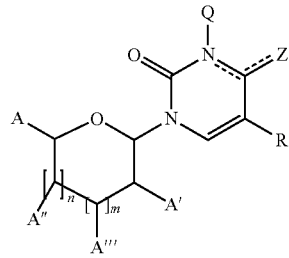

where, R (in the base) is selected from H, $C_1$-$C_4$ alkyl, halogen, OR, NHR (R=H, COCH₃, COO$^t$Bu); Q=H with the proviso that C—N double bond is absent, C—Z double bond is present and Z is O; Z is NH₂ with the proviso that C—Z double bond is absent, Q≠H; Z is O with the proviso that C—N double bond is absent;
A and A' are selected from H, lower alkyl-OH, —Oac, —CH₂OH, —CH₂OAc, —CH₂, OPiv, —CH₂OTBS;
m and n are integers 0,1;
A" and A'" are selected from 1,3-dihydroisobenzofuran (1a) or isochroman [3,4-dihydro-1H-benzo[c] pyran] represented by the formula (1b), where R, R', R" are selected from H, —OH, halo group, —CH₂OH, —CH₂OAc, —COOH, —COOMe, C1-C30 straight or branched alkyl group, optionally substituted with halogen or —OH or NH₂ or —NPhth; phenyl group optionally substituted with halogen, amino, nitro, C1-C6 alkyl;

with the proviso that when n=1[i.e(CH$_2$)n=1] and where m=0[i.e(CH$_2$)m=0], A''' is absent and A'' is 1,3-dihydro isobenzofuran (1a) or isochroman [3,4-dihydro-1H-benzo[c] pyran] represented by the formula (1b),

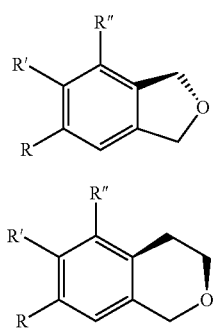

directly annulated at C-3, A and A' are selected from H, lower alkyl, OH, —OAc, —CH$_2$OH, —CH$_2$OAc, —CH$_2$OPiv, —CH$_2$OTBS; and R, R' and R'' in 1,3-dihydro isobenzofuran (1a) or isochroman [3,4-dihydro-1H-benzo[c] pyran] represented by the formula (1b) are selected from H, —OH, halo group, —CH$_2$OH, —CH$_2$OAc, —COOH, —COOMe, C1-C30 straight or branched alkyl group, optionally substituted with halogen or —OH or —NH$_2$ or —NPhth; phenyl group optionally substituted with halogen, amino, nitro, C1-C6 alkyl; R (in the base) is selected from H, C1-C4 alkyl, halogen; Q=H with the proviso that C—N double bond (....) is absent, C—Z double bond (....) is present and Z is O; Z is NH$_2$ with the proviso that C—Z double bond is absent, Q≠H; Z is O with the proviso that C—N double bond (....) is absent;

wherein the process comprises the steps of;
a) Preparing solution of diyne of formula

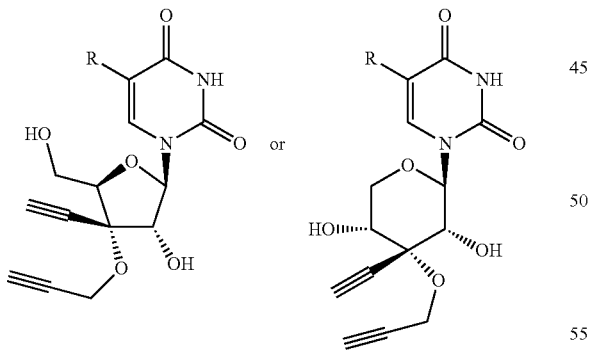

and alkyne in mole ratio ranging between 1:1 to 1:3 in a solvent followed by degassing of solution with dry argon;
b) adding a catalyst in mole ratio ranging between 0.02 to 0.05 into the degassed solution as obtained in step (a) followed by heating at temperature in the range of 70° C.-90° C. for a period in the range of 6 h-12 h;
c) cooling the solution as obtained in step (b) to room temperature ranging between 25° C.-30° C. followed by solvent evaporation and purification to obtain spiroannulated nucleoside;

wherein isochroman [3,4-dihydro-1H-benzo[c] pyran] is appended on the sugar moiety of the nucleoside via [2+2+2] cyclotrimerization reaction.

13. The process as claimed in claim 12, wherein said diyne used in step (a) is selected from the group consisting of furanoside nucleoside, pyranoside nucleoside (1-[3-C-phenylethynyl-3-O-(2-propynyl)-β-D-ribo-pentofuranosyl] uracil), (1-[3-C-(1-octynyl)-3-O-(2-propynyl)-β-D-ribo-pentofuranosyl]uracil), (1 [3-C-phenylethynyl-3-O-(2-propynyl)-β-D-ribopyranosyl]uracil), 1-[3-C-Propynyl/Phenylpropynyl/"Hexylpropynyl-3-O-(2-propynyl)-β-D-ribo-pentofuranosyl]5-flurouracil), (1 [3-C-Propynyl/Phenylpropynyl/"Hexylpropynyl-3-O-(2-propynyl)-β-D-ribopyranosyl]5-flurouracil).

14. A process for the preparation of Spiro annulated nucleoside of general Formula I;

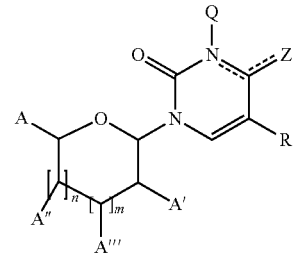

where, R (in the base) is selected from H, C$_1$-C$_4$ alkyl, halogen, OR, NHR (R=H, COCH$_3$, COO$^t$Bu); Q=H with the proviso that C—N double bond is absent, C—Z double bond is present and Z is O; Z is NH$_2$ with the proviso that C—Z double bond is absent, Q≠H; Z is O with the proviso that C—N double bond is absent;
A and A' are selected from H, lower alkyl-OH, —Oac, —CH$_2$OH, —CH$_2$OAc, —CH$_2$, OPiv, —CH$_2$OTBS;
m and n are integers 0,1;
A'' and A''' are selected from 1,3-dihydroisobenzofuran (1a) or isochroman [3,4-dihydro-1H-benzo[c] pyran] represented by the formula (1b), where R, R', R'' are selected from H, —OH, halo group, —CH$_2$OH, —CH$_2$OAc, —COOH, —COOMe, C1-C30 straight or branched alkyl group, optionally substituted with halogen or —OH or —NH2 or —NPhth; phenyl group optionally substituted with halogen, amino, nitro, C1-C6 alkyl;
with the proviso that when n=1[i.e(CH$_2$)n=1] and where m=0[i.e(CH$_2$)m=0], A''' is absent and A'' is 1,3-dihydro isobenzofuran (1a) or isochroman [3,4-dihydro-1H-benzo[c] pyran] represented by the formula (1b),

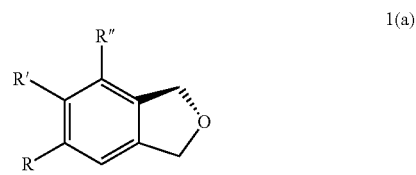

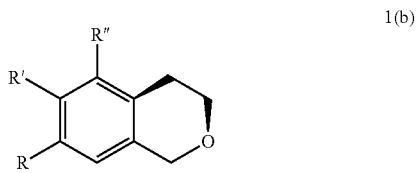

directly annulated at C-3, A and A' are selected from H, lower alkyl, OH, —OAc, —CH₂OH, —CH₂OAc, —CH₂OPiv, —CH₂OTBS; and R, R' and R" in 1,3-dihydro isobenzofuran (1a) or isochroman [3,4-dihydro-1H-benzo[c] pyran] represented by the formula (1b) are selected from H, —OH, halo group, —CH₂OH, —CH₂OAc, —COOH, —COOMe, C1-C30 straight or branched alkyl group, optionally substituted with halogen or —OH or —NH₂ or —NPhth; phenyl group optionally substituted with halogen, amino, nitro, C1-C6 alkyl; R (in the base) is selected from H, C1-C4 alkyl, halogen; Q=H with the proviso that C—N double bond (....) is absent, C—Z double bond (....) is present and Z is O; Z is NH₂ with the proviso that C—Z double bond is absent, Q≠H; Z is O with the proviso that C—N double bond (....) is absent;

wherein the process comprises the steps of;

a) Preparing solution of diyne of formula

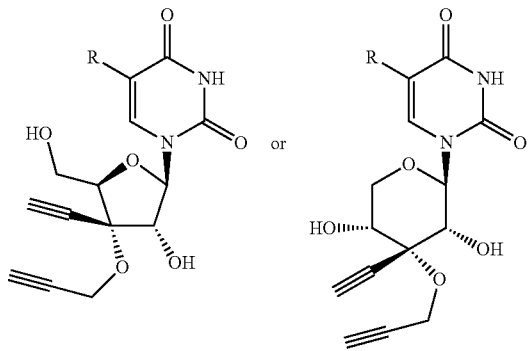

and alkyne in mole ratio ranging between 1:1 to 1:3 in a solvent followed by degassing of solution with dry argon;

b) adding a catalyst in mole ratio ranging between 0.02 to 0.05 into the degassed solution as obtained in step (a) followed by heating at temperature in the range of 70° C.-90° C. for a period in the range of 6 h-12 h;

c) cooling the solution as obtained in step (b) to room temperature ranging between 25° C.-30° C. followed by solvent evaporation and purification to obtain spiroannulated nucleoside;

wherein the spiroannulation of the nucleoside diyne with the symmetrical and unsymmetrical alkyne takes place at C-3 of the pyranoside ring.

15. The process as claimed in claim 14, wherein said diyne used in step (a) is selected from the group consisting of furanoside nucleoside, pyranoside nucleoside (1-[3-C-phenylethynyl-3-O-(2-propynyl)-β-D-ribo-pentofuranosyl] uracil), (1-[3-C-(1-octynyl)-3-O-(2-propynyl)-β-D-ribo-pentofuranosyl]uracil), (1 [3-C-phenylethynyl-3-O-(2-propynyl)-β-D-ribopyranosyl]uracil), 1-[3-C-Propynyl/Phenylpropynyl/"Hexylpropynyl-3-O-(2-propynyl)-β-D-ribo-pentofuranosyl]5-flurouracil), (1 [3-C-Propynyl/Phenylpropynyl/"Hexylpropynyl-3-O-(2-propynyl)-β-D-ribopyranosyl]5-flurouracil).

* * * * *